United States Patent [19]

Schülein et al.

[11] Patent Number: 5,919,691
[45] Date of Patent: Jul. 6, 1999

[54] ENZYME AND ENZYME PREPARATION WITH ENDOGLUCANASE ACTIVITY

[75] Inventors: Martin Schülein, Copenhagen Ø; Karen Margrethe Oxenbøll, Charlottenlund; Lene Nonboe Andersen, Birkerød; Søren Flensted Lassen, Copenhagen Ø; Markus Sakari Kauppinen, Copenhagen N; Jack Bech Nielsen, Hellerup, all of Denmark

[73] Assignee: Novo Nordisk A/S, Bagsvaerd, Denmark

[21] Appl. No.: 08/809,763

[22] PCT Filed: Oct. 6, 1995

[86] PCT No.: PCT/DK95/00400

§ 371 Date: Mar. 26, 1997

§ 102(e) Date: Mar. 26, 1997

[87] PCT Pub. No.: WO96/11262

PCT Pub. Date: Apr. 18, 1996

[30] Foreign Application Priority Data

Oct. 6, 1994 [DK] Denmark .................................. 1160/94
Nov. 11, 1994 [DK] Denmark .................................. 1296/94

[51] Int. Cl.[6] .............................. C12N 9/42; C12N 15/55
[52] U.S. Cl. ................... 435/209; 435/255.2; 435/256.1; 435/256.7; 435/320.1; 536/23.2
[58] Field of Search ........................... 435/320.11, 255.2, 435/256.1, 256.7, 209; 536/27.2

[56] References Cited

U.S. PATENT DOCUMENTS 4,562,150 12/1985 Yamanobe et al. ........................ 435/99

FOREIGN PATENT DOCUMENTS

WO 91/17243 11/1991 WIPO .
WO 91/17244 11/1991 WIPO .
WO 9311249 6/1993 WIPO .
WO 9407998 4/1994 WIPO .

OTHER PUBLICATIONS

Penicillium and Acremonium, vol. 1, Plenum Press, New York and London (1987), pp. 2–5.

Abstract (K–114)—Malburg et al., The xynB Gene from Fibrobacter succinogenes S85 Encodes a Xylanase which Possesses Endoglucanase and Cellobiosidase Activities (no date).

Chemical Abstracts, vol. 122, No. 3, Abstract No. 26388v (1995).

Dialog Information Services, file 5, Biosis, Dialog Accession No. 10520274, Biosis Accession No. 96120274. (1993).

EMBL, Gen Bank, DDBJ, Accession No. L29378. (1994).

EMBL, Gen Bank, DDBJ, Accession No. D63516. (1995).

EMBL, Gen Bank, DDBJ, Accession No. X76046. (1994).

Chemical Abstracts, vol. 102, No. 7, Abstract No. 60789y (1985).

Dalboge, H., et. al. (1994) Mol. Gen Genet. 243, 253–260.

Primary Examiner—Charles L. Patterson, Jr.
Attorney, Agent, or Firm—Steve T. Zelson, Esq.; Valeta A. Gregg, Esq.

[57] ABSTRACT

DNA sequences are disclosed encoding an enzyme exhibiting endoglucanase activity. The endoglucanase is useful in a variety of industrial processes requiring an alkaline cellulase.

16 Claims, No Drawings

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 590 base pairs
      (B) TYPE: nucleic acid
      (C) STRANDEDNESS: single
      (D) TOPOLOGY: linear (ii) MOLECULE TYPE: cDNA (v) FRAGMENT TYPE: N-terminal (vi) ORIGINAL SOURCE:
      (A) ORGANISM: Acremonium sp.
      (B) STRAIN: CBS 265.95

(xi) SEQUENCE DESCRIPTION: SEQ ID NO: 1:

```
AAAGCATCCA TTCGAGCCAG CAACCAAGAT GAAGTCTTCG ATTCTCGCCG GCATCTTCGC      60

CACGGGCGCC GTTGCCCAGA GTGGTGCTTG GGGACAGTGC GGTGGTAACG GATGGCAAGG     120

GGCGACTACC TGCGTGTCTG GCTATCACTG CGCTTACCAG AATGACTGGT ACAGCCAATG     180

CTTACCTGGC GATGCGTCGA CAACTTTGAA GACGTCGACG ACCACGGTCA AGCCCAGGGC     240

CACCAGCTCG GCGTCTCCTA CTACCAGCAG CTCGCCGGCC AAGGGCAAGT TCAAGTGGTT     300

CGGCATCAAC CAGTCCTGCG CCGAGTTCGG CACACCCACG TACCCCGGCA CCTGGGGCAA     360

GCACTTTACC TTCCCGTCAA CTGCTTCGAT CCAGACGCTC ATCAACGACG GATACAATAC     420

CTCCCGCGTG GCCTTTTCCA TGGAGCGTCT AGTGCCCGAC GTGTTGACAT CAACCACCTT     480

CGATGTCGGC TACCTCCGCA ACCTGACGGA GACGGTCGAC TTCATTACTA ACGTGGGGCG     540

CGTTCGCCGT GTCTATGGAC CCGCACAACT TACGGCCGGT TACTACGGCG                590
```

(2) INFORMATION FOR SEQ ID NO: 2:

(i) SEQUENCE CHARACTERISTICS:
      (A) LENGTH: 580 base pairs
      (B) TYPE: nucleic acid
      (C) STRANDEDNESS: single
      (D) TOPOLOGY: linear (ii) MOLECULE TYPE: cDNA (v) FRAGMENT TYPE: C-terminal (vi) ORIGINAL SOURCE:
    (A) ORGANISM: Acremonium sp.
    (B) STRAIN: CBS 265.95

(xi) SEQUENCE DESCRIPTION: SEQ ID NO: 2:

| | | | | | |
|---|---|---|---|---|---|
| GCACCAAGTA | ACCTGGAAAC | GGGACAAGCT | CCGGCACCAG | ACCCGGACTG | CGTCAGCGCC | 60 |
| GAGATTGGCG | TCCAGCGCGT | CGTCGGCGCC | ACCAGCTGTC | TGCGCGCCAA | CGGCAAGGTT | 120 |
| GGCATCATTG | GCGAGTTTGC | CGGCGGCCCA | ACTCAGTTTG | CCAGAACGCC | GTCACCGGCC | 180 |
| TCCTCGAGCA | CCTCAAGGCC | AACAGCGACG | TTGGCAAGGC | GCCCTCTGGT | GGGCCGTGCC | 240 |
| CTGGTGGGCG | GACTACATGT | ACTCGTTCGA | GCCTCCTTCG | GCACCGGGT | ACACCACCTA | 300 |
| CAACTCCATC | CTGAAGGAGT | ATGCCCCTTA | AAGGAGGTAT | TACGGCGGCC | ATTGGGCGAG | 360 |
| GCTCGATGGC | CTCAGCTCAG | AGTCCCCAAA | GAGGGATGGA | GATGGGGCGG | AGGCTCACGA | 420 |
| AATCCAACCC | TCATCTCCAT | CCAAAAGACG | CCAGAATGCT | AGAGAGAAAG | TTGGGAGCCA | 480 |
| TTGACGCATT | GACGGCACTT | CCATGTTACT | TTGACTAAAA | TTCGTTGTAC | ATACATAACT | 540 |
| ACATATTCTA | CCTTTCCAAA | AAAAAAAAAA | AAAAAAAAAA | | | 580 |

(2) INFORMATION FOR SEQ ID NO: 3:

(i) SEQUENCE CHARACTERISTICS:
    (A) LENGTH: 1511 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Acremonium sp.
    (B) STRAIN: CBS 265.95

(xi) SEQUENCE DESCRIPTION: SEQ ID NO: 3:

| | | | | | |
|---|---|---|---|---|---|
| AAAGCGCGTT | TCACTACCCG | TGTTATCAAG | ACTCGACACA | ATGGCTCGCG | GCGCTGCTCT | 60 |
| CTTCGGCCTG | GCCTCGCTCC | TCCTGGGCGC | GGTCAACGGC | CAGATGCCCG | GTGAGGGCGA | 120 |
| GGAGGTCCAC | CCCAAGATCA | ACACCTACCG | CTGCACCAAG | GGCGGCGGGT | GCAAGGAGAA | 180 |
| GACCAACTAC | GTCGTCCTCG | ATGCGCTCTT | CCACCCGGTC | ACCAGGGCA | ACAACGACTA | 240 |
| CGGTGCGGCG | AGTGGCGTCA | GAAGACCAAC | GCCACGGCCT | GCCGGAGCA | GGAGTCGTGC | 300 |
| GCCAAGGAAC | TTGCATCATG | GAGCCCGTCT | CCGACTACAG | CACCGGTGGT | GTGACCACCG | 360 |
| ACGGCGAACA | CCTCCGCCTG | CAGCAGCTGG | TCGACGGCAT | GCTCGTCACC | CCTCGCGTCT | 420 |
| ACCTCCTCGA | CGAGACCAAG | CGCCGCTACG | AGATGCTCTC | GCTCACCGGC | AACGAGTTCA | 480 |
| CCTTTGATGT | CGACGCCACC | AAGCTGCCCT | GCGGCATGAA | CAGCGCCCTC | TACCTCTCCG | 540 |
| AGATGAAGGC | CGACGGCGCC | CAGAGCACCC | TCAACCCCGG | CGGCGCCTAC | TTTGGCACCG | 600 |
| GCTACTGCGA | CGCCCAGTGC | TACATCACCC | CCTTCATCAA | CGGCCTCGGT | AACGTCGACG | 660 |
| GCAAGGGCGC | GTGCTGCAAC | GAGATGGACA | TCTGGGAGGC | CAACAAGCGG | GCCAACCACA | 720 |
| TCGCGCCGCA | CCCACTGCGAC | AAGAAGGGCC | CCTACCTCTG | CGAGGACGTC | GAGTGCGAGA | 780 |
| AGGAGGGCGT | GTGCGACAAG | ACCGGCTGCG | CGTGGAAACC | GTACCGGGTC | CACGTGACCG | 840 |
| ACTACTACGG | CGACGGCGAC | GAGTTCAAGT | CGACTCGTCC | CGGCTCTTCA | CCGTCGTCAC | 900 |
| CCAGTTCCAC | GCCAACCGCA | AGGGCAAGCT | CGAGTCCATC | CACCGCCTGT | ACGTGCAGGA | 960 |
| CGGCCAGGTC | ATCGAGTCGT | ACGTCGTCGA | CGCGCCGGGC | CTGACCCGTG | ACCGACAGCA | 1020 |

-continued

```
TGACCGACGA GCTCTGCGAG GTCACGGGCG CCGACGCCTT CATGCGCCTG GGCGCCATGC    1080

AGGGCATGGG CGAGGCCCTC ACCCGCGGCA TGGTCCTCGC GCTCAGCATC TGGTGGGACG    1140

AGGGCGGCAA CATGAACTGG CTGGACGCCG GCGAGGCCGG CCCCTGCAGC CTCGACGAGG    1200

GCCACCCGTC CAACATTGTC AAGGTCGAGC GCCGCCGCCG AGTCACCTTC AGCAACATGC    1260

GCTGGGGCGA GATCGACTCC ACCTACGAGA CCGGCGAGGA GGGCAAGGGC AAGGTTGGTA    1320

ACGGCAAGGG CAAGGGCAAG GGCAAGGGCA AGGAGTTCAA GAAGTAAACA GGTTCCCTTG    1380

GCCGAGTGTA ATTACTACCT GTAGAGAAGA GGGTGGTTAG AGGTCCAAAC ATATGACCAA    1440

TTGATCTTGA AAAAAAAAAA AAAAAAAAAA AAAAAAAAAA AAAAAAATGC GCCGCTCGAG    1500

CATCATCTAG A                                                         1511
```

(2) INFORMATION FOR SEQ ID NO: 4:

(i) SEQUENCE CHARACTERISTICS:
        (A) LENGTH: 1461 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Acremonium sp.
        (B) STRAIN: CBS 487.94

(xi) SEQUENCE DESCRIPTION: SEQ ID NO: 4:

```
AAAGTGATTG CCTGTCTTTC CGCCGTTGCA ATTGCTCCCA CTATGGCGCC TCTTTCAGTT      60

CATGCTGGCC TTGTGGCTCT CGTCGCCAGC TTGGCCATGG CGCAGAAGCC CATCAACGGC     120

GAGGACAACC ACCCTCCCCT CAAGACCTGG CGCTGCTCCC ATGCCGATGG CTGTGTCGAG     180

CACACCAACT ACATCGTCCT CGACTCCCTT GCCCATCCCG TCTACCAGGA GGGCACCGGC     240

GAGAGCTGCG GATCCTGGGG CAACCCTCCT CCCGTGGGAT GCCTGCCCGA ACCGCGAAGG     300

AGTGCGCTGA GAACTGCGTC ATGGAGGGCG GCAAGGACTA CTTCCGAATA TGGGATCGGA     360

GAACCGTTGG TGGATGCGCT TCAACCCTGT TACCAAGTTC GGTCGGACGG GCAAGTTCAA     420

AGTTCGCCCC GCGTCTACTT CTCGAGGAGA CGAGCAGAGT ACGAGATGTC ATCTACGGGG     480

CCGAGTTCAC TCGACGTCGA TGGTGATGCG CTCACCCTGT ACCAGCTCGT CGACGGCCAG     540

GTCAAGTCGC CCCGCGTCTA CCTTCTCGAC GAGACGAGCA AGCAGTACGA GATGTTCCAT     600

CTCACCGGCG CCGAGTCCAC CTTCGACGGG GATGCCTCGA AGTTGCCGTG TGGTATGAAC     660

AGTGCCCTGT ACCTGTCCGA GATGCTGGCG GATGGCGGCA AGAGCCCCTT GAACACTGGA     720

GGCGACAACT TGGCACCGGC TACTGCGATG CTCAGTGCTC ACAACCCCTT CATCACGGCG     780

AGGCAACATC GAGGGCTACG GCTCCTGCTG TGGTGAAATG GACATTTGGG AGGCCAACTC     840

CAGAGCCGTC CACGTCGCTC GCCACCCCTG CAACATCACC GAGCTCTACG AGTGCACCGG     900

CGACGAGTGC GCGTTCGAAG GCGTGTGCGA CAAGAGCGAC TGCGCCTGGA ACCCCTACCG     960

CGTCGACCAG GACGACTACT ACGACCGCGG CGATGAGTTC CGCGTCGACA CGAGCCGCCC    1020

CTTCACCGTC ATCACGACCT TCCCGGCCGA CGAGAACGGC AAGCTCACCA GCATCCACCG    1080

CACCTACGTC CAGGACGGCC GCCTCATCCG CAGCGAGGTC GTCAACAACC CCGACCTACC    1140

CCAGGTGAAC TACATGAACG ACGAGTTCTG CGACGCCACC GGCTCCCGGC GGTTCATGGA    1200

ACTCGGCGCC CACGAGGCCA TGGGCGACGC CATGACCCGC GGAATGTCCT GCCATCAGCC    1260

TCTGTGGACG CCGCGCAACA TCTGTGGATG GATGGCGCTT CGCAGAATGC GGCCCCTGC    1320
```

```
ATCGACACCG AGGGCAACCC GTCGAATATC GTCAAGGGTG AGCCCAACCC CGTCGTCACC        1380

CTCAGCAAAA TGAAGTGGGG TGAGATTGGC ACGACCTGGA AGGCGGATTG CGCGGCGCCG        1440

GCCAAGCTCA AGCTGTTCTA A                                                 1461

(2) INFORMATION FOR SEQ ID NO: 5:

(i) SEQUENCE CHARACTERISTICS:
        (A) LENGTH: 1965 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Acremonium sp.
        (B) STRAIN: CBS 487.94

(xi) SEQUENCE DESCRIPTION: SEQ ID NO: 5:

AAAGCATGAA GAGGACTCAG GCCGGACTTG CTCTGCTGCT CGCAGCTTCC GAGGGGGCTT          60

TCGCCCAGGT CTCGACCCCC TGGGGACAGT GCGGTGGCCT CAACTACAAC GGCCCGACCC         120

AGTGCCCGCC TGGATGGTAC TGCCAGTACT CCAACGATTG GTACTCCCAG TGCCTCCAGG         180

GCCACGCCAC GACGACCCTG TCCACGTCCA CCACGTCCAC GAGCTCCTCG TCTTCGTCTT         240

CGTCTTCCTC CTCGTCGTCG TCCTCTTCCT CTCGACCGTC TCTACGAGCT CGACTGTCTC         300

GACCACCTCC TCCGGACCCG GCCCGACCTC CTCCCCCGGC GTCTGCGGAG GCAGCTTCGA         360

GTTCCAGTCT GCCAACGACT GGGTTCAGTC CTCCAACCCC GGGTGGAACC TCGGCAACTC         420

TCTCGATGCC ATCCCCAACG AGGATTCCTG GAACAACGGG CCCGTCCAGG CCGAAGTCTT         480

TGACTACGCC GTCGAGCAGG GCTTCAAGAG CGTCCGCATC CCGGTCACCT ACACCCACCA         540

TCTCACCAGC GGCTCTCCCG ACTGGAAGAT CGACGAGGTC TGGCTCCAGC GCGTTCGAAG         600

ATGTCATCGA CGGGGCCTCG TCAGGGACTC TACGTCGTGA CAACGTCCAC CACGACTCCT         660

GGGAGTGGGC CGACGTCAAG CAGGCCCCGG GGCCGACATC GACGAGATCC AGGAGCGCTT         720

CGGTGCCATC TGGGCTCAGA TCGCCGACAA GCTCAAGTGC AAGTCGTCTC TCCTTTCGTT         780

CGAGTCCATC AACGAGGCCC CTGCCCACAA CGCCGCCGAG GGTGAGCTTG TCAACGAATT         840

CAACGACATC TTCCTCGAGG CCGTCGTCGC CTCCGGTGGT TCACACGGAG CGCGTTCTCC         900

AGTTCGCCAG CGGACACATT GCACCCATCA TGACGTCCCA GTGGTTCAGC ATCATTCACG         960

CCGAGGACGC CGCCGCTGGG AGTGGTTTGA CCACGTCGCG ACCGTCGCCA CCGAGCTGAC        1020

ACCGCGCTCG TGTCTGGGAC AACGGCCTGG ACCACCTCGA CCGCAACACC GGCATCTGGC        1080

GTGACCCCGT CTCCCTGGCG ATCGTTGACG CCGCCATCCG CGCGAGCGCA ACTCGCTCCC        1140

CGGCAGCACC ACCGATGCCA ACGCCGGCAC GCAGTTCAGC TCCGCCTTCG TCTGGAACCG        1200

CGTCGGCAAC GAGGTCGAGG ACTACGAGCT CCCCTGGCTC TTCAACGGCA ACACCCTCGT        1260

CAGCATCGAG ACCCATACGG GCGATGCCCT CTCCCAGGGC GCCGACTACA CGACGTCCGC        1320

CAACTCCATC ACCTGACCGA GAGCTTCCTC TCCCAGTACC TCGGCGCCGA TGTCTCGACC        1380

GAGCAGCAAG ACCAACCTCA CTCTTACCAT CTCCGCCGGC GCCTTTTCCC AGGTTGAGCT        1440

CATCCAGTGG GACACCCCCG AGCTGGTCGA TGAGCCCGAC GCCACTCCCG GCCAGGACCT        1500

TTGGATCGCC GTCCAGTGGA AGGGCTGGCG CATGGTTGCC GCCGTTCGTG CCCAGGCCCT        1560

CGACGGCACC ATCCTCTTCG ACGACTGGAG CCCAGTGGCT GCCCGCCCTG AAAGAGGGGT        1620

CGTGCGACCT TCAACTCCCA CTGGTTCTTC GAGGGCGACA ACCTCATCCT CAGGAGCGCC        1680

GCCATCGAAG CCGTCCTCGC CCTCGACAAG GCCGTCGAGT TCGAGTTCGA GTTCTACCCC        1740
```

```
CGCGTTCCCG GCAACTCGGT CACGTACCTC CTCGACCCGA ACCCCGAGGA GTGTTAAGCG     1800

GGCGATGAGG CGGGGGCGTG CTCGAGGCAC GATGCCCTGC GTGGCTGACT GACTCTCTTC     1860

TGAATGAGGA GGGGATGGTC TGCCCTGGCC CTTCACTGAA CGTACCTATC ATCGAGTCAT     1920

ACCGTAGAAA TACTAGTCCC TGATCTGATG AAAAAAAAAA AAAAA                    1965
```

(2) INFORMATION FOR SEQ ID NO: 6:

(i) SEQUENCE CHARACTERISTICS:
        (A) LENGTH: 1321 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Acremonium sp.
        (B) STRAIN: CBS 487.94

(xi) SEQUENCE DESCRIPTION: SEQ ID NO: 6:

```
AAAGCTCTAG TATGAAGTTC CTTGCTCTCA CCGCCCTTGC CGGAGGTGCT GTCGCCCAGT       60

CCGGCGCCTG GGGCCAGTGT GGCGGCAACG GATGGACGGG CCCAACGACA TGTGTCGCGG      120

GATACACTTG CACGTTCTCG AACCCGTGGT ATAGCCAGTG TCTTCCGGGA ACCGGTCCTC      180

CTCCCGTGAC CACTACTACT ACCAGCACCC AGACAACTCT CCGCACCACG ACGACGACAT      240

CGACTACCAC CAACACGCCT GGTCCGACCT CTCTTCCCGG CGAGTTTCCT GTGGTATGGT      300

ACCAACGTGG GCGGTGCCGA GTTTTGGGGG AGAACAAGCT GGCCGGGCAG GTGGGGGAAA      360

GGCACTTCAC CTTCCTGACC AATGCGATCA ATACCCTCCG CCGCGATGGC TACAACACCT      420

TCCGCGTCCA GTTCAAGATG GAGCGCCTGA GCCAACAGAG CCTGACGGGC GCCTTCAACC      480

AGGTATACCT CACCAACCTG ATCATCTCGA TCAACCAGGT CACGAGCACC GGCGCCTACG      540

CCGTGCTCGA CCCGCACATC TACGGCCGGT ACTTCGGTAA CGTCATCACC GACGTCGCAG      600

CTTTCCGGAC GTGGTGGCGC AACGTCGTGG CGCTGTTCGC ATCCAACCCG CGCGTCGTCT      660

CGACACAACA ACGAGTACCA CACGATGGAC CAGAACTCGT GTTCAACCTC ACCCAGACGA      720

CCATCGACGG CATCCGCGCG GCGGGGGCGG ACCAGTGGAT CTTCGTGGAG GGCAACCAGT      780

GGTCCGGGGC TTGGAGCTGT CCGGACGTCA ACGACAACAT GAAGAACCTG CAGGACCCGC      840

GCAACAAGAT CATCTACCAG ATGCACCAGT ACCTCGACTC GGACAGCTCG GGACCAGCC      900

CCAACTGCGT GTCCACGACC ATCGGGCGCG AGCGGCTGGT GGCGGCGACG AACTGGCTGC      960

GGGCCAACGG CAAGCTGGGC ATCCTGGGCG AGTTCGCGGG CGGCGCGAAC CAGAACTCCC     1020

GCACCGGCGG TTCAGGGGAT ACTGGACTAC CTCGAGGCCA ACGACGACGT GTGGAAGGGA     1080

TATCTCTGGT GGGCGGCGGG GCCCTGGTGG AACGACTACA TGTTCAACTT TGAGCCGCCC     1140

AGCGGTACGG GATACCAGTA CTACAACAGC CTGCTGAGGC AGTACATTCC TTGAGGTGGG     1200

ACACGGCTTC TGGCTTCTGG CTTCGGGCTC CAGACTGATG TACCTATATT TATCGTCTTC     1260

GCTGAGTCTG ATCAATAGCT ATCTACCTAA CTGACTCGAA AAAAAAAAA AAAAAAAAA      1320

A                                                                   1321
```

(2) INFORMATION FOR SEQ ID NO: 7:

(i) SEQUENCE CHARACTERISTICS:
        (A) LENGTH: 105 base pairs
        (B) TYPE: nucleic acid
        (C) STRANDEDNESS: single
        (D) TOPOLOGY: linear

```
    (ii) MOLECULE TYPE: cDNA (v) FRAGMENT TYPE: N-terminal (vi) ORIGINAL SOURCE:
         (A) ORGANISM: Acremonium sp.
         (B) STRAIN: CBS 487.94

(xi) SEQUENCE DESCRIPTION: SEQ ID NO: 7:

GTGGTGATCA TCTCGCGTCT CTCCCAAGAG CTGCTCATCA AGATGAAGGC CTTCGCGATC       60

CTCCCGTGCG CCACGGTCCT CGCCGACAGC TGGAAGAATG TCAAG                     105
```

ENZYME AND ENZYME PREPARATION WITH ENDOGLUCANASE ACTIVITY

This application is a 35 U.S.C. 371 national application of PCT/DK95/00400 filed Oct. 6, 1995 and claims priority under 35 U.S.C. 119 of Danish applications 1160/94 and 1296/94 filed Oct. 6, 1994 and Nov. 11, 1994, the contents of which are fully incorporated herein by reference.

The present invention relates to an enzyme composition, an isolated enzyme with cellulolytic (endoglucanase) activity at alkaline conditions, a DNA construct encoding the enzyme, a method of producing the enzyme or enzyme composition, a detergent composition comprising the enzyme or the composition, and use of the enzyme e.g. in the detergent industry, the textile industry and the paper pulp industry.

BACKGROUND OF THE INVENTION

Endoglucanases (EC No. 3.2.1.4) constitute a group of hydrolases, which catalyse endo hydrolysis of 1,4-β-D-glycosidic linkages in cellulose, cellulose derivatives (such as carboxy methyl cellulose and hydroxy ethyl cellulose), lichenin, β-1,4 bonds in mixed β-1,3 glucans such as cereal β-D-glucans or xyloglucans and other plant material containing cellulosic parts. The authorized name is endo-1,4-β-D-glucan 4-glucano hydrolase, but the abbreviated term endoglucanase is used in the present specification. Reference can be made to T. -M. Enveri, "Microbial Cellulases" in W. M. Fogarty, Microbial Enzymes and Biotechnology, Applied Science Publishers, p. 183–224 (1983); Methods in Enzymology, (1988) Vol. 160, p. 200–391 (edited by Wood, W. A. and Kellogg, S. T.); Béguin, P., "Molecular Biology of Cellulose Degradation", Annu. Rev. Microbiol. (1990), Vol. 44, pp. 219–248; Béguin, P. and Aubert, J -P., "The biological degradation of cellulose", FEMS Microbiology Reviews 13 (1994) p.25–58; Henrissat, B., "Cellulases and their interaction with cellulose", Cellulose (1994), Vol. 1, pp. 169–196. Celluloses are found in connection with many gums and they are components of cell walls in e.g. fruits, vegetables and cereals.

Endoglucanases have been found to be produced by various types of organisms such as plants and microorganisms, and endoglucanases of a wide variety of specificities have been identified.

Fungal endoglucanases have been described by Sheppard, P.O., et al., "The use of conserved cellulase family-specific sequences to clone Cellulase homologue cDNAs from *Fusarium oxysporum*, Gene, (1994), Vol. 15, pp. 163–167, Saloheimo, A., et al., "A novel, small endoglucanase gene, egl5, from *Trichoderrma reesei* isolated by expression in yeast", Molecular Microbiology (1994), Vol. 13(2), pp. 219–228; van Arsdell, J. N. et al, (1987), Cloning, characterization, and expression in *Saccharomyces cerevisiae* of endoglucanase I from *Trichoderma reesei*, Bio/Technology 5: 60–64; Penttilä, M. et al., (1986), "Homology between cellulase genes of *Trichoderma reesei*: complete nucleotide sequence of the endoglucanase I gene", Gene 45:253–263; Saloheimo, M. et al, (1988), "EGIII, a new endoglucanase from *Trichoderma reesei*: the characterization of both gene and enzyme", Gene 63:11–21; Gonzáles, R., et al., "Cloning, sequence analysis and yeast expression of the egll gene from *Trichoderma longibrachiatum*", Appl. Microbiol. Biotechnol., (1992), Vol. 38, pp. 370–375; Ooi, T. et al. "Cloning and sequence analysis of a cDNA for cellulase (FI-CMCase) from *Aspergillus aculeatus*", Curr. Genet., (1990), Vol. 18, pp. 217–222; Ooi, T. et al, "Complete nucleotide sequence of a gene coding for *Asper-gillus aculeatus* cellulase (FI-CMCase)", Nucleic Acids Research, (1990), Vol. 18, No. 19, p. 5884; Xue, G. et al., "Cloning and expression of multiple cellulase cDNAs from the anaerobic rumen fungus *Neocallimastix patriciarum* in *E. coli*", J. Gen. Microbiol., (1992), Vol. 138, pp. 1413–1420; Xue, G. et al., "A novel polysaccharide hydrolase cDNA (celD) from *Neocallimastix patriciarum* encoding three multi-functional catalytical domains with high endoglucanase, cellobiohydrolase and xylanase activities", J. Gen. Microbiol., (1992), Vol. 138, pp. 2397–2403; Zhou, L. et al., "Intronless celB from the anaerobic fungus *Neocallimastix patriciarum* encodes a modular family A endoglucanase", Biochem. J., (1994), Vol. 297, pp. 359–364; Dalbæge, H. and Heldt-Hansen, H. P., "A novel method for efficient expression cloning of fungal enzyme genes", Mol. Gen. Genet., (1994), Vol. 243, pp. 253–260; Ali, B. R. S. et al., "Cellulases and hemicellulases of the anaerobic fungus Piromyces constitute a multiprotein cellulose-binding complex and are encoded by multigene families", FEMS Microbiol. Lett., (1995), Vol. 125, No. 1, pp. 15–21.

WO 91/17243 (Novo Nordisk A/S) discloses a cellulase preparation consisting of a homogenous endoglucanase component immunoreactive with an antibody raised against a highly purified 43 kDa endoglucanase derived from *Humicola insolens*, DSM 1800.

WO 91/17244 (Novo Nordisk A/S) discloses a new (hemi)-cellulose degrading enzyme, such as an endoglucanase, a cellobiohydrolase or a β-glucosidase, which may be derived from fungi other that Trichoderma and Phanerochaete.

WO 93/20193 discloses an endoglucanase derivable from *Aspergillus aculeatus*.

WO 94/00578 (Commonwealth Scientific and Industrial Research Organisation) describes a method for cloning a cellulase with the activity of anaerobic rumen fungi, which includes *Neocallimastix patriciarum*.

WO 94/14953 (Novo Nordisk A/S) describes a fungal endoglucanase for degrading or modifying plant cell wall components, e.g. for producing wine or juice etc. The endoglucanase may be derived from *Aspergillus aculeatus*, CBS 101.43.

WO 94/21801 (Genencor Inc.) concerns a cellulase system isolated from *Trichoderma longibranchiatum* exhibiting endoglucanase activity.

WO 94/26880 (Gist Brocades N. V.) discloses an isolated mixture of cellulose degrading enzymes, which preferable are obtained from Trichoderma, Aspergillus or Disporotrichum, comprising endoglucanase, cellobiohydrolase, and xyloglucanase activity.

WO 95/02043 (Novo Nordisk A/S) describes an enzyme with endoglucanase activity derived from *Trichoderma harzianum*, which can be used for a number of purposes including e.g. degradation or modification of plant cell walls.

Kang, M. G., Park, H. M., Kim, Y. S, Lee, J. R., Kim, Y. K., Lee, Y. H.: Abstract from 94th General Meeting, American society Microbiology, K-112, 1994, discloses the strain Cephalosporium sp., RYM-202, and the purification of 3 cellulases (EC 3.2.1.4, P-I, P-II, P-III) having optimum pH values in the alkaline range.

In Peberdy, J. F., (1987), is disclosed that Cephalosporium species are generally speaking now renamed Acremonium with some exceptions.

Endoglucanases are widely used industrially, e.g. within the detergent industry, in the textile industry, in paper pulp processing and in the food and feed industry.

There is an ever existing need for providing novel endoglucanases, preferably in single-component or mono-component form, which may be used for applications where a single or dominating endoglucanase activity is desirable.

The object of the present invention is to provide novel enzymes having substantial cellulolytic activity at alkaline conditions and improved performance in paper pulp processing, textile treatment, laundry processes and/or in animal feed; preferably novel mono-component cellulases, more preferably mono-component endoglucanases, which may be produced by recombinant techniques.

SUMMARY OF THE INVENTION

It has now surprisingly been found that an enzyme composition exhibiting high cellulolytic (endoglucanase) activity at alkaline conditions, i.e. a cellulase enzyme, is producible by or derivable from fungi of the genus Acremonium which fungi are not immunologically cross-reactive with antibodies raised against *Humicola insolens*, DSM 1800, *Fusarium-oxysporum*, DSM 2672, *Myceliopthora thermophile*, CBS 117.65, and *Cephalosporium* sp., RYM-202.

Since the fungal organisms belonging to Acremonium (or Cephalosporium) are generally known as capable of producing antibiotics, the cellulase should preferably be produced by recombinant techniques, i.e. should be cloned and expressed.

Thus, more specifically, the present invention relates to novel cellulases which are derivable from or producible by fungi selected from the group of strains consisting of Acremonium sp., Cephalosporium sp., *Acremonium acremonium, Acremonium persicinum, Acremonium brachypenium, Acremonium dichromosporum, Acremonium obclavatum, Acremonium pin-kertoniae, Acremonium roseogriseum, Acremonium incoloratum*, and *Acremonium furatum*, especially Acremonium sp., CBS 478.94, Acremonium sp., CBS 265.95, *Acremonium persicinum*, CBS 169.65, *Acremonium acremonium*, AHU 9519, Cephalosporium sp., CBS 535.71, *Acremonium brachypenium*, CBS 866.73, *Acremonium dichromosporum*, CBS 683.73, *Acremonium obclavatum*, CBS 311.74, *Acremonium pinkertoniae*, CBS 157.70, *Acremonium roseogriseum*, CBS 134.56, *Acremonium incoloratum*, CBS 146.62, and *Acremonium furatum*, CBS 299.70H.

Further, the present invention relates to a DNA construct comprising a DNA sequence encoding an enzyme exhibiting endoglucanase activity, which DNA sequence comprises the N-terminal DNA sequence shown in SEQ ID No. 1 and the C-terminal DNA sequence shown in SEQ ID No. 2, and/or the DNA sequence obtainable from the plasmid in *Saccharomyces cerevisiae* DSM 10076, or an analogue thereof; or which DNA sequence comprises the DNA sequence shown in SEQ ID No. 3, and/or the DNA sequence obtainable from the plasmid in *Saccharonmyces cerevisiae* DSM 9969, or an analogue thereof; or which DNA sequence comprises the DNA sequence shown in SEQ ID No. 4, and/or the DNA sequence obtainable from the plasmid in *Saccharomyces cerevisiae* DSM 9977, or an analogue thereof; or which DNA sequence comprises the DNA sequence shown in SEQ ID No. 5, and/or the DNA sequence obtainable from the plasmid in Saccharomyces cerevisiae DSM 10077, or an analogue thereof; or which DNA sequence comprises the DNA sequence shown in SEQ ID No. 6, and/or the DNA sequence obtainable from the plasmid in *Saccharomyces cerevisiae* DSM 10079, or an analogue thereof; or which DNA sequence comprises the N-terminal (partial) DNA sequence shown in SEQ ID No. 7, and/or the DNA sequence obtainable from the plasmid in *Saccharomyces cerevisiae* DSM 10084, or an analogue thereof. The DNA sequences obtainable from the plasmid(s) in DSM 10076 and DSM 9969 have Acremonium sp., DSM 265.95, as the donor organism. The DNA sequences obtainable from the plasmid (s) in DSM 9977, DAM 10077, DSM 10079 and DSM 10084 have Acremonium sp., DSM 487.94, as the donor organism.

The enzyme composition and the isolated or cloned and expressed cellulase of the invention may be useful in any industrial process requiring an alkaline cellulase, e.g. for providing localised variation in the colour density of dyed fabric such as stone-washing of denim, for improving the drainage of an aqueous suspension of paper pulp, for the de-inking of recycled paper, in detergent compositions and in fabric softeners.

DETAILED DESCRIPTION OF THE INVENTION

In the primary screening of fungal sources which may be capable of producing an enzyme with substantial cellulytic activity at alkaline conditions, the screening for fungal sources (obtained e.g. from soil) may be carried out by soil dilution, direct inoculation by soil dust, small particles or plant roots on solid Chapek and Hetchinson media, and the species may be identified by inoculation of isolated culture on a conventional solid medium in petri dishes. Then, the presence of cellulolytic activity may be qualitatively estimated by visual observation of fungal growth on filter paper or formation of clear zones on solid media containing amorphous cellulose. Further, the presence of cellulase activity under alkaline conditions may be estimated by 7–10 days of cultivation on agar-amorphous acid swollen cellulose at 28° C., installation of block into agar HEC-LAS (linear alkylbenzene sulphonate, concentration 0.12–0.24%) at pH 9–10.6 and incubation at 40° C. for ½–2 days, and visual detection of cellulolytic activity by observing a white clearing zone in the blue stained HES (1% AZCL-HEC solution obtained from Megazyme, Australia).

In a preferred embodiment, the present invention relates to an enzyme composition which is derived from or producible by fungi selected from the genus Acremonium. More preferred, the invention relates to an enzyme composition having endoglucanase activity which is derived from or producible by fungi selected from the group consisting of the species Acremonium sp., *Acremonium persicinum, Acremonium brachypenium, Acremonium dichromosporum, Acremonium obclavatum, Acremonium pinkertoniae, Acremonium roseogriseum, Acremonium incoloratum*, and *Acremonium furatum*. Examples of useful strains are Acremonium sp., CBS 478.94, Acremonium sp., CBS 265.95, *Acremonium persicinum*, CBS 169.65, *Acremonium acremonium*, AHU 9519, Cephalosporium sp., CBS 535.71, *Acremonium brachypenium*, CBS 866.73, *Acremonium dichromosporum*, CBS 683.73, *Acremonium obclavatum*, CBS 311.74, *Acremonium pinkertoniae*, CBS 157.70, *Acremonium roseogriseum*, CBS 134.56, *Acremonium incoloratum*, CBS 146.62, and *Acremonium furatum*, CBS 299.70H.

The strains *Acremonium persicinum*, CBS 169.65, *Acremonium acremonium*, AHU 9519, *Acremonium brachypenium*, CBS 866.73, *Acremonium dichromosporum*, CBS 683.73, *Acremonium obclavatum*, CBS 311.74, *Acremonium pinkertoniae*, CBS 157.70, *Acremonium roseogriseum*, CBS 134.56, *Acremonium incoloratum*, CBS 146.62, and *Acremonium furatum*, CBS 299.70H and *Cephalosporium* sp., CBS 535.71, are all believed to be commercially available strains which were published in the catalogue of the relevant depositary institution at the priority date of this patent application.

The strain which was deposited on 28 Sep. 1994 at Centraalbureau voor Schimmelcultures under number CBS 478.94 in accordance with the provisions of the Budapest Treaty belongs to *Acremonium* sp. The culture is characterized by a hyaline mycelium and the formation of individually occurring erect and slender phialides, from which hyaline conidia are produced. The phialides are delimited by a distinct basal septum. The conidia are ellipsoid (0.5–1)× (1–2) $\mu$m. These observations are based on a culture grown on YPG-agar.

The strain which was deposited on 7 Apr. 1995 at Centraalbureau voor Schimmelcultures under number CBS 265.95 in accordance with the provisions of the Budapest Treaty belongs to *Acremonium* sp.

The Enzyme

In the present context, the term "cellulolytic activity" refers to the ability of the enzyme to degrade cellulose to glucose, cellobiose, triose and other cello-oligosaccharides.

This ability may be determined by the formation of clearing zones in a carboxymethyl cellulose (CMC) gel under the conditions specified below.

In the present context the term "enzyme" is understood to include a mature protein or a precursor form thereof as well to a functional fragment thereof which essentially has the activity of the full-length enzyme. Furthermore, the term "enzyme" is intended to include homologues of said enzyme. Such homologues comprise an amino acid sequence exhibiting a degree of identity of at least 60% with the amino acid sequence of the parent enzyme, i.e. the parent cellulase. The degree of identity may be determined by conventional methods, see for instance, Altshul et al., *Bull. Math. Bio.* 48: 603–616, 1986, and Henikoff and Henikoff, *Proc. Natl. Acad. Sci. USA* 89: 10915–10919, 1992. Briefly, two amino acid sequences are aligned to optimize the alignment scores using a gap opening penalty of 10, a gap extension penalty of 1, and the "blosum 62" scoring matrix of Henikoff and Henikoff, supra.

Alternatively, the homologue of the enzyme may be one encoded by a nucleotide sequence hybridizing with an oligonucleotide probe prepared on the basis of the nucleotide sequence or an amino acid sequence under the following conditions: presoaking in 5×SSC and prehybridizing for 1 hr. at about 40° C. in a solution of 20% formamide, 5×Denhardt's solution, 50 mM sodium phosphate, pH 6.8, and 50 $\mu$g denatured sonicated calf thymus DNA, followed by hybridization in the same solution supplemented with 100 $\mu$M ATP for 18 hrs. at about 40° C., followed by a wash in 0.4×SSC at a temperature of about 45° C.

Molecules to which the oligonucleotide probe hybridizes under these conditions are detected using standard detection procedures (e.g. Southern blotting).

Homologues of the present enzyme may have one or more amino acid substitutions, deletions or additions. These changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al. , *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active enzyme. Amino acids essential to the activity of the enzyme of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for cellulolytic activity to identify amino acid residues that are critical to the activity of the molecule. Sites of ligand-receptor interaction can also be determined by analysis of crystal structure as determined by such techniques as nuclear magnetic resonance, crystallography or photoaffinity labelling. See, for example, de Vos et al., *Science* 255: 306–312, 1992; Smith et al.,*J. Mol. Biol.* 224: 899–904, 1992; Wlodaver et al., *FEBS Lett.* 309: 59–64, 1992.

The homologue may be an allelic variant, i.e. an alternative form of a gene that arises through mutation, or an altered enzyme encoded by the mutated gene, but having substantially the same activity as the enzyme of the invention. Hence mutations can be silent (no change in the encoded enzyme) or may encode enzymes having altered amino acid sequence.

The homologue of the present enzyme may also be a genus or species homologue, i.e. an enzyme with a similar activity derived from another species.

A homologue of the enzyme may be isolated by preparing a genomic or cDNA library of a cell of the species in question, and screening for DNA sequences coding for all or part of the homologue by using synthetic oligonucleotide probes in accordance with standard techniques, e.g. as described by Sambrook et al., *Molecular Cloning:A Laboratory Manual*, 2nd. Ed. Cold Spring Harbor Laboratory, Cold Spring Harbor, *New York*, 1989, or by means of polymerase chain reaction (PCR) using specific primers as described by Sambrook et al., supra.

The enzyme of the invention is in isolated form, i.e. provided in a condition other than its native environment which is soil, possibly Mongolian soils. In a preferred form, the isolated enzyme is substantially free of other proteins, particularly other enzymes of fungal origin. The enzyme of the present invention may, for instance, be isolated from fungi from the genus Acremonium, provided that the enzyme is not immunologically cross-reactive with antibodies raised against endoglucanases (EC 3.2.1.4) from *Humicola insolens*, DSM 1800, *Fusarium oxysporum*, DSM 2672, *Myceliopthora thermophile*, CBS 117.65, or *Cephalosporium* sp., RYM-202. In one embodiment, the enzyme of the present invention is obtainable from the supernatant of *Acremonium* sp., *Acremonium persicinum, Acremonium acremonium*, *Cephalosporium* sp., *Acremonium brachypenium, Acremonium dichromosporum, Acremonium obclavatum, Acremonium pinkertoniae, Acremonium roseogriseum, Acremonium incoloratum*, and *Acremonium furatum*.

The isolated enzyme may be characterized by e.g. SDS-PAGE and assayed using procedures known in the art. For example, the enzyme of the invention has a pH optimum above about 7, more preferably above about 8, especially above about 9.

Further, the isolated enzyme and the enzyme composition of the invention preferably have a relative activity at pH 10 of at least 50% as compared to the activity at pH 8.5, the activity being measured in Savi U units on a suitable substrate.

Preferably, the isolated enzyme and the enzyme composition of the invention are stable in the presence of sodium linear alkylbenzene sulphonate, sodium polyoxyethylene alkyl sulphate, sodium dodecyl sulphate, sodium α-olefin sulphonate, sodium alkyl sulphonate, and α-sulpho-fatty acid ester.

It may be preferred to provide the enzyme in a highly purified form, i.e. greater than 90% pure, more preferably 95% and most preferably 99% pure, as determined by SDS-PAGE.

In a further aspect, the present invention relates to a DNA construct comprising a DNA sequence encoding an enzyme exhibiting endoglucanase activity, which DNA sequence comprises a) the N-terminal DNA sequence shown in SEQ ID No. 1 and the C-terminal DNA sequences shown in SEQ ID No. 2, and/or the DNA sequence obtainable from the plasmid in *Saccharomyces cerevisiae* DSM 10076, or b) an analogue of the N-terminal DNA sequence shown in SEQ ID No. 1 and the C-terminal DNA sequences shown in SEQ ID No. 2 and/or the DNA sequence obtainable from the plasmid in *Saccharomyces cerevisiae* DSM 10076, which i) is homologous with the N-terminal DNA sequence shown in SEQ ID No. 1 and the C-terminal DNA sequences shown in SEQ ID No. 2 and/or the DNA sequence obtainable from the plasmid in *Saccharomyces cerevisiae* DSM 10076, or ii) hybridizes with the same oligonucleotide probe as the N-terminal DNA sequence shown in SEQ ID No. 1 and the C-terminal DNA sequences shown in SEQ ID No. 2 and/or the DNA sequence obtainable from the plasmid in *Saccharomyces cerevisiae* DSM 10076, or iii) encodes a polypeptide which is homologous with the polypeptide encoded by a DNA sequence comprising the N-terminal DNA sequence shown in SEQ ID No. 1 and the C-terminal DNA sequences shown in SEQ ID No. 2 and/or the DNA sequence obtainable from the plasmid in *Saccharomyces cerevisiae* DSM 10076, or iv) encodes a polypeptide which is immunologically reactive with an antibody raised against the purified endoglucanase encoded by the N-terminal DNA sequence shown in SEQ ID No. 1 and the C-terminal DNA sequences shown in SEQ ID No. 2 and/or obtainable from the plasmid in *Saccharomyces cerevisiae*, DSM 10076.

It is believed that the N-terminal and C-terminal partial DNA sequences shown in SEQ ID No. 1 and 2, respectively, are identical to the corresponding partial DNA sequences obtainable from the plasmid in *Saccharomyces cerevisiae*, DSM 10076.

The strain *Saccharomyces cerevisiae* was deposited under the deposition number DSM 10076 on 30 Jun. 1995 at the DSM—Deutsche Sammlung von Mikroorganismen und Zellkulturen GmbH, Maascheroder Weg 1b, D-38125 Braunschweig, Germany, according to the Budapest Treaty.

In yet a further aspect, the present invention relates to a DNA construct comprising a DNA sequence encoding an enzyme exhibiting endoglucanase activity, which DNA sequence comprises a) the DNA sequence shown in SEQ ID No. 3 and/or the DNA sequence obtainable from the plasmid in *Saccharomyces cerevisiae* DSM 9969, or b) an analogue of the DNA sequence shown in SEQ ID No. 3 and/or the DNA sequence obtainable from the plasmid in *Saccharomyces cerevisiae* DSM 9969, which i) is homologous with the DNA sequence shown in SEQ ID No. 3 and/or the DNA sequence obtainable from the plasmid in *Saccharomyces cerevisiae* DSM 9969, or ii) hybridizes with the same oligonucleotide probe as the DNA sequence shown in SEQ ID No. 3 and/or the DNA sequence obtainable from the plasmid in *Saccharomyces cerevisiae* DSM 9969, or iii) encodes a polypeptide which is homologous with the polypeptide encoded by a DNA sequence comprising the DNA sequence shown in SEQ ID No. 3 and/or the DNA sequence obtainable from the plasmid in *Saccharomyces cerevisiae* DSM 9969, or iv) encodes a polypeptide which is immunologically reactive with an antibody raised against the purified endoglucanase encoded by the DNA sequence shown in SEQ ID No. 3 and/or obtainable from the plasmid in *Saccharomyces cerevisiae*, DSM 9969.

It is believed that the DNA sequence shown in SEQ ID No. 3 is identical to the corresponding partial DNA sequences obtainable from the plasmid in *Saccharomyces cerevisiae*, DSM 9969.

The strain *Saccharomyces cerevisiae* was deposited under the deposition number DSM 9969 on 11 May 1995 at the DSM—Deutsche Sammlung von Mikroorganismen und Zellkulturen GmbH, Maascheroder Weg 1b, D-38125 Braunschweig, Germany, according to the Budapest Treaty.

In yet a further aspect, the present invention relates to a DNA construct comprising a DNA sequence encoding an enzyme exhibiting endoglucanase activity, which DNA sequence comprises a) the DNA sequence shown in SEQ ID No. 4, and/or the DNA sequence obtainable from the plasmid in *Saccharomyces cerevisiae* DSM 9977, or b) an analogue of the DNA sequence shown in SEQ ID No. 4 and/or the DNA sequence obtainable from the plasmid in *Saccharomyces cerevisiae* DSM 9977, which i) is homologous with the DNA sequence shown in SEQ ID No. 4 and/or the DNA sequence obtainable from the plasmid in *Saccharomyces cerevisiae* DSM 9977, or ii) hybridizes with the same oligonucleotide probe as the DNA sequence shown in SEQ ID No. 4 and/or the DNA sequence obtainable from the plasmid in *Saccharomyces cerevisiae* DSM 9977, or iii) encodes a polypeptide which is homologous with the polypeptide encoded by a DNA sequence comprising the DNA sequence shown in SEQ ID No. 4 and/or the DNA sequence obtainable from the plasmid in *Saccharomyces cerevisiae* DSM 9977, or iv) encodes a polypeptide which is immunologically reactive with an antibody raised against the purified endoglucanase encoded by the DNA sequence shown in SEQ ID No. 4 and/or obtainable from the plasmid in *Saccharomyces cerevisiae*, DSM 9977.

It is believed that the DNA sequence shown in SEQ ID No. 4 is identical to the corresponding partial DNA sequences obtainable from the plasmid in *Saccharomyces cerevisiae*, DSM 9977.

The strain *Saccharomyces cerevisiae* was deposited under the deposition number DSM 9977 on 11 May 1995 at the DSM—Deutsche Sammlung von Mikroorganismen und Zellkulturen GmbH, Maascheroder Weg 1b, D-38125 Braunschweig, Germany, according to the Budapest Treaty.

In yet a further aspect, the present invention relates to a DNA construct comprising a DNA sequence encoding an enzyme exhibiting endoglucanase activity, which DNA sequence comprises a) the DNA sequence shown in SEQ ID No. 5, and/or the DNA sequence obtainable from the plasmid in *Saccharomyces cerevisiae* DSM 10077, or b) an analogue of the DNA sequence shown in SEQ ID No. 5 and/or the DNA sequence obtainable from the plasmid in *Saccharomyces cerevisiae* DSM 10077, which i) is homologous with the DNA sequence shown in SEQ ID No. 5 and/or the DNA sequence obtainable from the plasmid in *Saccharomyces cerevisiae* DSM 10077, or ii) hybridizes with the same oligonucleotide probe as the DNA sequence shown in SEQ ID No. 5 and/or the DNA sequence obtainable from the plasmid in *Saccharomyces cerevisiae* DSM 10077, or iii) encodes a polypeptide which is homologous with the polypeptide encoded by a DNA sequence comprising the DNA sequence shown in SEQ ID No. 5 and/or the DNA sequence obtainable from the plasmid in *Saccharomyces cerevisiae* DSM 10077, or iv) encodes a polypeptide which is immunologically reactive with an antibody raised against the purified endoglucanase encoded by the DNA sequence shown in SEQ ID No. 5 and/or obtainable from the plasmid in *Saccharomyces cerevisiae*, DSM 10077.

It is believed that the DNA sequence shown in SEQ ID No. 5 is identical to the corresponding partial DNA sequences obtainable from the plasmid in *Saccharomyces cerevisiae*, DSM 10077.

The strain *Saccharomyces cerevisiae* was deposited under the deposition number DSM 10077 on 30 June 1995 at the DSM—Deutsche Sammlung von Mikroorganismen und Zellkulturen GmbH, Maascheroder Weg 1b, D-38125 Braunschweig, Germany, according to the Budapest Treaty.

In yet a further aspect, the present invention relates to a DNA construct comprising a DNA sequence encoding an enzyme exhibiting endoglucanase activity, which DNA sequence comprises a) the DNA sequence shown in SEQ ID No. 6, and/or the DNA sequence obtainable from the plasmid in *Saccharomyces cerevisiae* DSM 10079, or b) an analogue of the DNA sequence shown in SEQ ID No. 6 and/or the DNA sequence obtainable from the plasmid in *Saccharomyces cerevisiae* DSM 10079, which i) is homologous with the DNA sequence shown in SEQ ID No. 6 and/or the DNA sequence obtainable from the plasmid in *Saccharomyces cerevisiae* DSM 10079, or ii) hybridizes with the same oligonucleotide probe as the DNA sequence shown in SEQ ID No. 6 and/or the DNA sequence obtainable from the plasmid in *Saccharomyces cerevisiae* DSM 10079, or iii) encodes a polypeptide which is homologous with the polypeptide by a DNA sequence comprising the DNA sequence shown in SEQ ID No. 6 and/or the DNA sequence obtainable from the plasmid in *Saccharomyces cerevisiae* DSM 10079, or iv) encodes a polypeptide which is immunologically reactive with an antibody raised against the purified endoglucanase encoded by the DNA sequence shown in SEQ ID No. 6 and/or obtainable from the plasmid in *Saccharomyces cerevisiae*, DSM 10079.

It is believed that the DNA sequence shown in SEQ ID No. 6 is identical to the corresponding partial DNA sequences obtainable from the plasmid in *Saccharomyces cerevisiae*, DSM 10079.

The strain *Saccharomyces cerevisiae* was deposited under the deposition number DSM 10079 on 30 Jun. 1995 at the DSM—Deutsche Sammlung von Mikroorganismen und Zellkulturen GmbH, Maascheroder Weg 1b, D-38125 Braunschweig, Germany, according to the Budapest Treaty.

In yet a further aspect, the present invention relates to a DNA construct comprising a DNA sequence encoding an enzyme exhibiting endoglucanase activity, which DNA sequence comprises a) the N-terminal DNA sequence shown in SEQ ID No. 7, and/or the DNA sequence obtainable from the plasmid in *Saccharomyces cerevisiae* DSM 10084, or b) an analogue of the N-terminal DNA sequence shown in SEQ ID No. 7 and/or the DNA sequence obtainable from the plasmid in *Saccharomyces cerevisiae* DSM 10084, which i) is homologous with the N-terminal DNA sequence shown in SEQ ID No. 7 and/or the DNA sequence obtainable from the plasmid in *Saccharomyces cerevisiae* DSM 10084, or ii) hybridizes with the same oligonucleotide probe as the N-terminal DNA sequence shown in SEQ ID No. 7 and/or the DNA sequence obtainable from the plasmid in *Saccharomyces cerevisiae* DSM 10084, or iii) encodes a polypeptide which is homologous with the polypeptide encoded by a DNA sequence comprising the N-terminal DNA sequence shown in SEQ ID No. 7 and/or the DNA sequence obtainable from the plasmid in *Saccharomyces cerevisiae* DSM 10084, or iv) encodes a polypeptide which is immunologically reactive with an antibody raised against the purified endoglucanase encoded by the N-terminal DNA sequence shown in SEQ ID No. 7 and/or obtainable from the plasmid in *Saccharomyces cerevisiae*, DSM 10084.

It is believed that the N-terminal partial DNA sequence shown in SEQ ID No. 7 is identical to the corresponding partial DNA sequences obtainable from the plasmid in *Saccharomyces cerevisiae*, DSM 10084.

The strain *Saccharomyces cerevisiae* was deposited under the deposition number DSM 10084 on 30 Jun. 1995 at the DSM—Deutsche Sammlung von Mikroorganismen und Zellkulturen GmbH, Maascheroder Weg 1b, D-38125 Braunschweig, Germany, according to the Budapest Treaty.

In the present context, the "analogue" of the partial DNA sequences shown in SEQ ID No. 1 or 2 or 3 or 4 or 5 or 6 is intended to indicate any DNA sequence encoding an enzyme exhibiting endoglucanase activity, which has any or all of the properties i)–iv). The analogous DNA sequence a) may be isolated from another or related (e.g. the same) organism producing the enzyme with endoglucanase activity on the basis of the DNA sequences shown in SEQ ID No. 1 or 2 or 3 or 4 or 5 or 6, e.g. using the procedures described herein, and thus, e.g. be an allelic or species variant of the DNA sequence comprising the DNA sequences shown herein, b) may be constructed on the basis of the DNA sequences shown in SEQ ID No. 1 or 2 or 3 or 4 or 5 or 6, e.g. by introduction of nucleotide substitutions which do not give rise to another amino acid sequence of the endoglucanase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological (i.e. endoglucanase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The endoglucanase encoded by the DNA sequence of the DNA construct of the invention may comprise a cellulose binding domain (CBD) existing as an integral part of the encoded enzyme, or a CBD from another origin may be introduced into the endoglucanase enzyme.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for DNA sequence comparison: GAP creation penalty of 5.0 and GAP extension penalty of 0.3, the coding region of the DNA sequence exhibits a degree of identity preferably of at least 40%, more preferably at least 50%, more preferably at least 60%, more preferably at least 70%, even more preferably at least 80%, especially at least 90%, with the coding region of the (full or partial) DNA sequences shown in SEQ ID No. 1 or 2 or 3 or 4 or 5 or 6 or 7, respectively, or the DNA sequence(s) obtainable from the plasmid in *Saccharomyces cerevisiae*, DSM 10076, DSM 9969, DSM 9977, DSM 10077, DSM 10079 or DSM 10084, respectively.

The hybridization referred to in ii) above is intended to indicate that the analogous DNA sequence hybridizes to the same probe as the DNA sequence encoding the endoglucanase enzyme under certain specified conditions which are described in detail in the Materials and Methods section hereinafter. Normally, the analogous DNA sequence is highly homologous to the DNA sequence such as at least 70% homologous to the (full or partial) DNA sequences shown in SEQ ID No. 1 or 2 or 3 or 4 or 5 or 6 or 7, respectively, encoding an endoglucanase of the invention, such as at least 75%, at least 80%, at least 85%, at least 90% or even at least 95% homologous to said DNA sequence.

The homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for polypeptide sequence comparison: GAP creation penalty of 3.0 and GAP extension penalty of 0.1, the polypeptide encoded by an analogous DNA sequence exhibits a degree of identity preferably of at least 70%, more preferably at least 80%, especially at least 90%, with the enzyme encoded by a DNA construct comprising the (full or partial) DNA sequence shown in SEQ ID No. 1 or 2 or 3 or 4 or 5 or 6 or 7, respectively, or the DNA sequence obtainable from the plasmid in *Saccharomyces cerevisiae*, DSM 10076, DSM 9969, DSM 9977, DSM 10077, DSM 10079 or DSM 10084, respectively.

In connection with property iv) above it is intended to indicate an endoglucanase encoded by a DNA sequence isolated from strain DSM 10076 or DSM 9969 or DSM 9977 or DSM 10077 or DSM 10079 or DSM 10084, respectively, and produced in a host organism transformed with said DNA sequence or produced by the strain DSM 10076 or DSM 9969 or DSM 9977 or DSM 10077 or DSM 10079 or DSM 10084, respectively. The immunological reactivity may be determined by the method described in the Materials and Methods section below.

In further aspects the invention relates to an expression vector harbouring a DNA construct of the invention, a cell comprising the DNA construct or expression vector and a method of producing an enzyme exhibiting endoglucanase activity which method comprises culturing said cell under conditions permitting the production of the enzyme, and recovering the enzyme from the culture.

In a still further aspect the invention relates to an enzyme exhibiting endoglucanase activity, which enzyme a) is encoded by a DNA construct of the invention
b) produced by the method of the invention, and/or
c) is immunologically reactive with an antibody raised against a purified endoglucanase encoded by the (full or partial) DNA sequence shown in SEQ ID No. 1 or 2 or 3 or 4 or 5 or 6 or 7, respectively, or the DNA sequence obtainable from the plasmid in *Saccharomyces cerevisiae*, DSM 10076 or DSM 9969 or DSM 9977 or DSM 10077 or DSM 10079 or DSM 10084, respectively.

The endoglucanase mentioned in c) above may be encoded by the DNA sequence isolated from the strain *Saccharomyces cerevisiae*, DSM 10076 or DSM 9969 or DSM 9977 or DSM 10077 or DSM 10079 or DSM 10084, respectively, and produced in a host organism transformed with said DNA sequence or produced by the strain DSM 10076 or DSM 9969 or DSM 9977 or DSM 10077 or DSM 10079 or DSM 10084, respectively.

Expression Cloning in Yeast

The DNA sequence of the invention encoding an enzyme exhibiting endoglucanase activity may be isolated by a general method involving cloning, in suitable vectors, a DNA library from Acremonium sp., especially from Acremonium sp., CBS 478.94 or CBS 265.95, transforming suitable yeast host cells with said vectors, culturing the host cells under suitable conditions to express any enzyme of interest encoded by a clone in the DNA library, screening for positive clones by determining any endoglucanase activity of the enzyme produced by such clones, and isolating the enzyme encoding DNA from such clones.

The general method is further disclosed in WO 94/14953 the contents of which are hereby incorporated by reference. A more detailed description of the screening method is given in Example 6 below.

The DNA sequence coding for the enzyme may for instance be isolated by screening a cDNA library of Acremonium sp., and selecting for clones expressing the appropriate enzyme activity (i.e. endoglucanase activity) or from *Saccharomyces cerevisiae*, DSM 10076 or DSM 10077 or DSM 10079 or DSM 10084, each deposited under the Budapest Treaty on 30 Jun., 1995, at DSM (Deutsche Sammlung von Mikroorganismen und Zellkulturen GmbH, Mascheroder Weg 16, D-38124 Braunschweig, Germany) or from *Saccharomyces cerevisiae*, DSM 9969 or DSM 9977, each deposited under the Budapest Treaty on 11 May, 1995, at DSM (Deutsche Sammlung von Mikroorganismen und Zellkulturen GmbH). The appropriate DNA sequence may then be isolated from the clone by standard procedures, e.g. as described in Example 6.

It is expected that a DNA sequence coding for a homologous enzyme, i.e. an analogous DNA sequence, is obtainable from other microorganisms. For instance, the DNA sequence may be derived by similarly screening a cDNA library of another fungus, such as a strain of an Aspergillus sp., in particular a strain of *A. aculeatus* or *A. niger*, a strain of Trichoderma sp., in particular a strain of *T. reesei, T. viride, T. longibrachiatum, T. harzianum* or *T. koningii* or a strain of a Fusarium sp., in particular a strain of *F. oxysporum*, or a strain of a Humicola sp., or a strain of a Neocallimastix sp., a Piromyces sp., a Penicillium sp., an Agaricus sp., or a Phanerochaete sp.

Alternatively, the DNA coding for a endoglucanase of the invention may, in accordance with well-known procedures, conveniently be isolated from DNA from a suitable source, such as any of the above mentioned organisms, by use of synthetic oligonucleotide probes prepared on the basis of a DNA sequence disclosed herein. For instance, a suitable oligonucleotide probe may be prepared on the basis of the nucleotide sequence shown in any of the (full or partial) sequences listed in SEQ ID No. 1, 2, 3, 4, 5 or 6 or 7, respectively, or any suitable subsequence thereof.

A wide range of indicator systems for the different types of enzymes may be used for the screening of yeast colonies on agar plates. For instance, cellulases and endoglucanases may be identified by clearing zones in carboxymethyl cellulose after staining with Congo Red.

Nucleic Acid Construct

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding an enzyme of interest. The construct may optionally contain other nucleic acid segments.

The nucleic acid construct encoding the enzyme of the invention may suitably be of genomic or cDNA origin, for instance obtained by preparing a genomic or cDNA library and screening for DNA sequences coding for all or part of the enzyme by hybridization using synthetic oligonucleotide probes in accordance with standard techniques (cf. Sambrook et al., supra).

The nucleic acid construct encoding the enzyme may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., *Science* 239 (1988), 487–491.

The nucleic acid construct is preferably a DNA construct which term will be used exclusively in this specification and claims.

Recombinant Vector

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130). For filamentous fungi, selectable markers include amdS, pyrG, arqB, niaD, sC.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

For secretion from yeast cells, the secretory signal sequence may encode any signal peptide which ensures efficient direction of the expressed enzyme into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., *Yeast* 6, 1990, pp. 127–137).

For efficient secretion in yeast, a sequence encoding a leader peptide may also be inserted downstream of the signal sequence and upstream of the DNA sequence encoding the enzyme. The function of the leader peptide is to allow the expressed enzyme to be directed from the endoplasmic reticulum to the Golgi apparatus and further to a secretory vesicle for secretion into the culture medium (i.e. exportation of the enzyme across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an Aspergillus sp. amylase or glucoamylase, a gene encoding a *Rhizomucor miehei* lipase or protease, a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

The procedures used to ligate the DNA sequences coding for the present enzyme, the promoter and optionally the terminator and/or secretory signal sequence, respectively, and to insert them into suitable vectors containing the information necessary for replication, are well known to persons skilled in the art (cf., for instance, Sambrook et al., op.cit.).

Host Cells

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a cDNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, or gram-negative bacteria such as *Echerichia coli*. The transformation of the bacteria may be effected by protoplast transformation or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous enzymes therefrom are described, e.g. in U.S. Pat. No. 4,599,311, U.S. Pat. No. 4,931,373, U.S. Pat. No. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the enzyme of the invention may be preceded by a signal sequence and optionally a leader sequence, e.g. as described above. Further examples of suitable yeast cells are strains of Kluyveromyces, such as *K. lactis*, Hansenula, e.g. *H. polymorpha*, or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger*. The use of Aspergillus spp. for the expression of proteins is described in, e.g., EP 272 277, EP 230 023. The transformation of *F. oxysporum* may, for instance, be carried out as described by Malardier et al., 1989, Gene 78: 147–156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

The transformed or transfected host cell described above is then cultured in a suitable nutrient medium under conditions permitting the expression of the present enzyme, after which the resulting enzyme is recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The enzyme produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of enzyme in question.

In a still further aspect, the present invention relates to treatment of cellulose or cellulosic material with an enzyme preparation, which is enriched in an enzyme exhibiting endoglucanase activity as described above.

For example, the enzyme preparation of the present invention is useful for the degradation or modification of plant cell wall containing materials, said preparation being enriched in an enzyme with endoglucanase activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast or Celluzyme (all available from Novo Nordisk A/S). In the present context, the term "enriched" is intended to indicate that the endoglucanase activity of the enzyme preparation has been increased, e.g. with an enrichment factor of at least 1.1, conveniently due to addition of an enzyme of the invention prepared by the method described above.

Alternatively, the enzyme preparation enriched in an enzyme with cellulolytic (endoglucanase) activity may be one which comprises an enzyme of the invention as the major enzymatic component, e.g. a mono-component enzyme preparation.

The screening and expression cloning may be carried out using the following:

MATERIALS AND METHODS

Donor organism: mRNA was isolated from Acremonium sp., CBS 478.94, and Acremonium sp., CBS 265.95, respectively, grown in a cellulose-containing fermentation medium with agitation to ensure sufficient aeration. Mycelia were harvested after 4–6 days' growth, immediately frozen in liquid nitrogen and stored at −80° C.

Yeast strains: The *Saccharomyces cerevisiae* strain used was yNG231 (MAT α, leu2, ura3–52, his4–539, pep4-delta 1, cir+) or JG169 (MATα; ura 3–52; leu 2–3, 112; his 3-D200; pep 4-1137; prc1::HIS3; prb1:: LEU2; cir+).

Plasmids: The expression plasmid pYHD17 containing the yeast TPI promoter was prepared from the commercially available plasmid pYES 2.0 (Invitrogen). The plasmid and the construction thereof is further described in WO 93/11249, the contents of which is hereby incorporated by reference.

The Aspergillus expression vector pHD414 is a derivative of the plasmid p775 (described in EP 238 023). The construction of pHD414 is further described in WO 93/11249.

Extraction of total RNA was performed with guanidinium thiocyanate followed by ultracentrifugation through a 5.7M CsCl cushion, and isolation of poly(A)$^+$ RNA was carried out by oligo(dT)-cellulose affinity chromatography using the procedures described in WO 94/14953.

cDNA synthesis and modification: Double-stranded cDNA was synthesized from 5 μg of poly(A)$^+$ RNA by the RNase H method (Gubler & Hoffman 1983, Sambrook et al., 1989) using the hair-pin modification. The procedure is further described in WO 95/02043. After having been treated with mung bean nuclease (Bethesda Research Laboratories), the ds cDNA was blunt-ended with T4 DNA polymerase (Invitrogen) and the cDNA was ligated to non-palindromic BstX I adaptors (Invitrogen) as described in WO 95/02043.

Construction of cDNA libraries: The adapted, ds cDNA was recovered by centrifugation, washed in 70% EtOH and resuspended in 25 ml H$_2$O. Prior to large-scale library ligation, four test ligations were carried out in 10 μl of ligation buffer (same as above) each containing 1 μl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either pYES 2.0 vector Invitrogen or pYHD17).

Using the optimal conditions a large-scale ligation was set up in 40 μl of ligation buffer. One μl aliquots were transformed into electrocompetent E. coli 1061 cells, and the transformed cells were titered and the library plated on LB + ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. For further details reference is made to WO 95/02043.

Construction of yeast libraries: To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Φ, 1.5 kV, 25 μF) into 40 μl competent S. cerevisiae JG 169 cells (OD600=1.5 in 500 ml YPD, washed twice in cold DIW, once in cold 1M sorbitol, resuspended in 0.5 ml 1M sorbitol, (Becker & Guarante, 1991). After addition of 1 ml 1M cold sorbitol, 80 μl aliquots were plated on SC+glucose−uracil agar plates to give 250–500 c.f.u./plate and incubated at 30° C. for 3–5 days.

Identification of positive colonies: After 3–5 days of growth, the agar plates were replica plated onto several sets of SC+galactose-uracil agar plates. One set of the replica plates contained 0.1% AZCL HE cellulose. These plates were incubated for 3–7 days at 30° C. Endoglucanase positive colonies were identified as colonies surrounded by a blue halo.

Cells from enzyme-positive colonies were spread for single colony isolation on agar, and an enzyme-producing single colony was selected for each of the endoglucanase-producing colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical).

Isolation of a cDNA gene for expression in Aspergillus: One or more endoglucanase-producing yeast colonies was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 μl water. The DNA was transformed into E. coli by standard procedures. Plasmid DNA was isolated from E. coli using standard procedures, and analyzed by restriction enzyme analysis. The cDNA insert was excised using appropriate restriction enzymes and ligated into an Aspergillus expression vector.

Transformation of Aspergillus oryzae or Aspergillus niger Protoplasts may be prepared as described in WO 95/02043, p. 16, line 21–page 17, line 12, which is hereby incorporated by reference.

100 μl of protoplast suspension is mixed with 5–25 μg of the appropriate DNA in 10 μl of STC (1.2M sorbitol, 10 mM Tris-HCl, pH =7.5, 10 mM $CaCl_2$). Protoplasts are mixed with p3SR2 (an A. nidulans amdS gene carrying plasmid). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on minimal plates (Cove, Biochem. Biophys. Acta 113 (1966) 51–56) containing 1.0M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of A. Oryzae Transformants

Each of the transformants were inoculated in 10 ml YPM and propagated. After 2–5 days of incubation at 37° C., 10 ml supernatant was removed. The endoglucanase activity was identified by AZCL HE cellulose or AZCL β-glucan as described above.

Hybridization Conditions (to be used in evaluating property i) of the DNA construct of the invention): Suitable conditions for determining hybridization between an oligonucleotide probe and an "analogous" DNA sequence involves presoaking of the filter containing the DNA fragments to hybridize in 5×SSC and prehybridizing for 1 h at ~50° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~50° C. followed by washing three times in 2×SSC, 0.2% SDS at 50° C. for 30 minutes.

A suitable oligonucleotide probe to be used in the hybridization may be prepared on the basis of the DNA sequence shown in SEQ ID No. 1 (or 2 or 3 or 4 or 5 or 6 or 7).

Immunological cross-reactivity: Antibodies to be used in determining immunological cross-reactivity may be prepared by use of a purified endoglucanase. More specifically, antiserum against the endoglucanase of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-URA agar: SC-URA, 20 g/l agar added.

AZCL β-glucan, AZCL xyloglucan, AZCL HE cellulose (Megazyme, Australia).

Uses

Detergent Compositions

According to the invention, the cellulase may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes such as amylase, lipase, cutinase, protease, peroxidase, and oxidase, e.g. laccase).

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $Na_2SO4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol,7 EO, or $C_{12-15}$alcohol,5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |

-continued

| | |
|---|---|
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol,7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate-/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O,2SiO_2$) | 0–6% |
| Sodium citrate | 4–8% |
| Sodium percarbonate | 13–22% |
| TAED | 3–8% |
| Polymers (e.g. polycarboxylates and PVP= | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The cellulase of the invention may be incorporated in concentrations conventionally employed in detergents. It is at present contemplated that, in the detergent composition of the invention, the cellulase may be added in an amount corresponding to 0.00001–1 mg (calculated as pure enzyme protein) of cellulase per liter of wash liquor.

Pulp and Paper Applications

In the papermaking pulp industry, the enzyme preparation according to the invention may be applied advantageously e.g. as follows:

For debarking: pretreatment with the enzyme preparation according to the invention may degrade the cambium layer prior to debarking in mechanical drums resulting in advantageous energy savings.

For defibration: treatment of a material containing cellulosic fibers with the enzyme preparation of the invention prior to refining or beating may result in reduction of the energy consumption due to the hydrolysing effect of the cellulase on the interfibre surfaces. Use of the enzyme preparation of the invention may result in improved energy savings as compared to the use of known enzymes, since it is believed that the enzyme composition of the invention may possess a higher ability to penetrate fibre walls.

For fibre modification, i.e. improvement of fibre properties where partial hydrolysis across the fibre wall is needed which requires deeper penetrating enzymes (e.g. in order to make coarse fibers more flexible). Deep treatment of fibers has so far not been possible for high yield pulps e.g. mechanical pulps or mixtures of recycled pulps. This has been ascribed to the nature of the fibre wall structure that prevents the passage of enzyme molecules due to physical restriction of the pore matrix of the fibre wall. It is contemplated that the enzyme composition of the invention is capable of penetrating into the fibre wall.

For drainage improvement. The drainability of papermaking pulps may be improved by treatment of the pulp with hydrolysing enzymes, e.g. cellulases. Use of the enzyme preparation according to the invention may be more effective, e.g. result in a higher degree of loosening bundles of strongly hydrated micro-fibrils in the fines fraction (consisting of fibre debris) that limits the rate of drainage by blocking hollow spaces between fibers and in the wire mesh of the paper machine. The Canadian standard freeness (CSF) increases and the Schopper-Riegler drainage index decreases when pulp in subjected to cellulase treatment, see e.g. U.S. Pat. No. 4,923,565; TAPPI T227, SCAN C19:65 which are hereby incorporated by reference.

For inter fibre bonding. Hydrolytic enzymes are applied in the manufacture of papermaking pulps for improving the inter fibre bonding. The enzymes rinse the fibre surfaces for impurities e.g. cellulosic debris, thus enhancing the area of exposed cellulose with attachment to the fibre wall, thus improving the fibre-to-fibre hydrogen binding capacity. This process is also referred to as dehornification. Paper and board produced with a cellulase containing enzyme preparation according to the invention may have an improved strength or a reduced grammage, a smoother surface and an improved printability. These improvements are believed to be a result of the improved penetrability of the modified/derivatised enzyme(s).

For enzymatic deinking. Partial hydrolysis of recycled paper during or upon pulping by use of hydrolysing enzymes such as cellulases are known to facilitate the removal and agglomeration of ink particles. Use of the enzyme preparation according to the invention may give a more effective loosening of ink from the surface structure due to a better penetration of the enzyme molecules into the fibrillar matrix of the fibre wall, thus softening the surface whereby ink particles are effectively loosened. The agglomeration of loosened ink particles are also improved, due to a more efficient hydrolysis of cellulosic fragments found attached to ink particles originating from the fibres.

The treatment of lignocellulosic pulp may, e.g., be performed as described in WO 91/14819, WO 91/14822, WO 92/17573 and WO 92/18688.

Textile Applications

In another embodiment, the present invention relates to use of the enzyme preparation according to the invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulolytic and mechanical action is required. It is also known that "super-softness" is achievable when the treatment with cellulase is combined with a conventional treatment with softening agents. It is contemplated that use of the enzyme preparation of the invention for bio-polishing of cellulosic fabrics is advantageous, e.g. a more thorough polishing can be achieved. Bio-polishing may be obtained by applying the method described e.g. in WO 93/20278.

Stone-Washing

It is known to provide a "stone-washed" look (localized abrasion of the colour) in dyed fabric, especially in denim fabric or jeans, either by washing the denim or jeans made from such fabric in the presence of pumice stones to provide the desired localized lightening of the colour of the fabric or by treating the fabric enzymatically, in particular with cellulolytic enzymes. The enzyme treatment may be carried out either alone such as disclosed U.S. Pat. No. 4,832,864, together with a smaller amount of pumice than required in the traditional process, or together with perlite such as disclosed in WO 95/09225.

Determination of Cellulolytic Activity

Cellulolytic enzymes hydrolyse CMC, thereby increasing the viscosity of the incubation mixture. The resulting reduction in viscosity may be determined by a vibration viscosimeter (e.g. MIVI 3000 from Sofraser, France). Determination of the cellulolytic activity, measured in terms of S-CEVU, may be determined according to the assay described below:

The S-CEVU assay quantifies the amount of catalytic activity present in the sample by measuring the ability of the sample to reduce the viscosity of a solution of carboxymethylcellulose (CMC). The assay is carried out at 40° C.;

pH 7.5; 0.1M phosphate buffer; time 30 min; using a relative enzyme standard for reducing the viscosity of the CMC substrate (carboxymethylcellulose Hercules 7 LFD); enzyme concentration approx. 0.15 S-CEVU/ml.

Further, 1 Savi U (unit) is defined as the amount of enzyme capable of forming 1 μmole of glucose equivalents per minute.

The invention is further illustrated by the following non-limiting examples.

EXAMPLE 1
Identification of Relationship with Alkaline Cellulases from *Humicola Insolens*, DSM 1800

The Ochterlony immunodiffusion test was used for identification of the relationship of the strains Acremonium sp., CBS 265.95, Acremonium sp., CBS 478.94, *Acremonium persicinum*, CBS 169.65, *Acremonium acremonium*, AHU 9519, and Cephalosporium sp., CBS 535.71 with alkaline cellulases from *Humicola insolens*, DSM 1800.

Antisera were raised by the Applicant against the *Humicola insolens*, DSM 1800, strain and used in dilutions from 1 to ¹⁄₁₆. Blocks of fungi grown on amorphous cellulose-agar medium were inserted into the wells of 0.9% Bacto-agar-PBST (Phosphate Buffer Saline) adjusted by NaOH to pH 7.4 containing 0.5 ml of Tween 20 per litre of PBST. Around the blocks induced by cellulase fungi, other wells were filled with other dilutions of antisera (from 1 to 1/16). Small petri dishes were inserted into larger dishes with wet wadding to protect against drying-out and were incubated at 37° C. over-night.

None of the blocks containing Acremonium sp., CBS 265.95, Acremonium sp., CBS 478.94, *Acremonium persicinum*, CBS 169.65, *Acremonium acremonium*, AHU 9519, and Cephalosporium sp., CBS 535.71 formed precipitation arcs with the antisera.

EXAMPLE 2
Determination of Alkaline Cellulase Activity on Amorphous Cellulose
Materials and Methods:

Substrate preparation: 20 gram acid-swollen AVICEL stock solution (see below for a preparation which can be stored for one month) was centrifuged for 20 min. at 5000 rpm, the supernatant was poured off, and the sediment was resuspended in 30 ml of buffer. Then the suspension was centrifuged for 20 min. at 5000 rpm, the supernatant was poured off, and the sediment was resuspended in buffer to a total of 30 g. This corresponds to a substrate concentration of 10 g AVICEL/l.

Buffer: 0.1M Barbital at pH 8.5 or 0.1M Glycine at pH 10.0

Enzyme Solution:

The enzymes were diluted to an activity of 0.2-1 S-CEVU/ml at pH 8.5 or pH 10.0.

Reagents:

2% NaOH, PHBAH-reagent: 1.5 g of p-hydroxy benzoic acid hydrazide and 5.0 g sodium tartrate was dissolved in 100 ml of 2% NaOH. The substrate, the buffer and the enzyme solution were mixed to a final substrate concentration of 4.00 g/l.

Preparation of Acid Swollen Cellulose:
Materials:
5 g Avicel (Art. 2331 Merck)
150 ml 85% ortho-phosphoric acid (Art. 573 Merck)
400 ml acetone (Art. 14 Merck)
1.3 l deionized water (Milli Q)
1 l glass beaker
1 l glass filter funnel
2 l suction flask
Ultra Turrax Homogenizer
Procedure:

Acetone and phosphoric acid was cooled on ice. 5 g Avicel was moistened with water, then 150 ml of ice cold 85% ortho-phosphoric acid was added, and the mixture was placed on ice bath with weak stirring for 1 h. 100 ml of ice cold acetone was added with stirring, followed by transfer of the mixture to a glass filter funnel, followed by washing with 3×100 ml ice cold acetone and dry suction after each washing. The filter cake was washed with 2×500 ml water and sucked as dry as possible after each wash. The filter cake was resuspended to a total volume of 300 ml and blended to homogeneity (using the Ultra Turrax Homogenizer).

The resulting product was stored in a refrigerator.

The substrate/buffer solution was preheated for 5 min at 40° C. Then the enzyme solution was added and the solution was whirlmixed for 5 sec., followed by incubation for 20 min. at 40 ° C. The reaction was stopped by adding 500 μl 2% NaOH solution, followed by whirlmixing for 5 sec. The samples were centrifuged for 20 min. at 5000 rpm. 1000 μl of supernatant was transferred from the test tubes to new test tubes, and 500 μl PHBAH-reagent was added, followed by boiling for 10 min. The test tubes were cooled in ice water.

The absorbance of the samples were measured on a spectrophotometer at 410 nm.
Standard Glucose Curve:

A stock solution containing 300 mg/l was diluted to 5, 10, 15 and 25 mg/l, respectively. 1000 μl of the diluted standards were mixed with 500 μl of PHBAH-reagent and were treated as the other samples, see above.

Definition:

1 Savi U (unit) is defined as the amount of enzyme capable of forming 1 μmole of glucose equivalents per minute.

Determination of activity: The release of reducing glucose equivalent was calculated using the standard curve.

The results are shown in the table below.

The strain mentioned in the table below were grown in shaking flasks in a substrate consisting of:

Rofec (from Roquette) 10 g/l
$NH_4NO_3$ 10 g/l
$KH_2PO_4$ 10 g/l
Solcafloc 40 g/l
$MgSO_4$, $7H_2O$ 0.75 g/l
Pluronic 100% 0.1 ml
Water ad 1000 ml The activity was measured in S-CEVU/ml.

TABLE

| Enzyme compositions (strain) | (Activity) S-CEVU/ml | Savi U/ml pH 8.5 | Savi U/ml pH 10 |
|---|---|---|---|
| Acremonium sp., CBS 265.95 | 55 | 4.4 | 2.2 |
| Acremonium sp., CBS 478.94 | 22 | 2.5 | 1.9 |
| Cephalosporium sp., CBS 535.71 | 116 | 3.8 | 2.3 |
| *Acremonium persicinum*, CBS 169.65 | 63 | 3.5 | 2.1 |
| *Acremonium acremonium*, AHU 9519 | 23 | — | — |

EXAMPLE 3
Preparation of Alkaline Cellulase Powder

Cellulase powder preparations according to the invention was prepared by cultivation of the following Acremonium strains, respectively: A. brachypenium, CBS 866.73, A. dichromosporum, CBS 683.73/ ATCC 32181, A. obclavatum, CBS 311.74, A. pinkertoniae, CBS 157.70, A. roseogriseum, CBS 134.56, A. incoloratum, CBS 146.62/ATCC 14613, and A. furatum, CBS 299.70H.

Each cellulase preparation was prepared as follows: A YPG agarslant was used as seed culture medium. An agar piece of spores grown on agar plate was inoculated to a 500 ml volume Erlenmeyer flask with 2 bafflers containing 100 ml culture medium. Cultivation for 48 hours at 27° C. 3 ml of this seed culture were then inoculated to a main culture medium consisting of 4% wheat bran and 0.1% Tween 80, at pH 6.7, again in 100 ml total fluid in 500 ml Erlenmeyer shake flask. Cultivation for 5 days at 27° C. on a shaking table. 25 shake flask was used and the broth filtrates was collected through sintered glass filter to avoid adsorption to cellulosic material.

The filtrate was concentrated on an Amicon ultrafiltration unit with a membrane with a cut off at 10 kD to ⅕ of the original volume and freeze dried.

The activity was measured in S-CEVU/mg.

TABLE (Activity)

| Enzyme compositions (strain) | S-CEVU/mg |
| --- | --- |
| Acremonium brachypenium, CBS 866.73 | 48 |
| Acremonium dichromosporum, CBS 683.73 | 62 |
| Acremonium obclavatum, CBS 311.74 | 693 |
| Acremonium pinkertoniae, CBS 157.70 | 550 |
| Acremonium roseogriseum, CBS 134.56 | 38 |
| Acremonium incoloratum, CBS 146.62 | 132 |
| Acremonium furatum, CBS 299.70H | 82 |

EXAMPLE 4
Performance of Cellulase from Acremonium Strains in Detergent Compositions
Materials and Methods Apparatus: Terg-o-tometer
Liquid volume: 100 ml
Agitation: 150 movements/min with vertical stirrer
Rinse time: 10 min in running tapwater
Washing temp: 40° C.
Washing liquor: 6.5 g/l of powder detergent, European type (Ariel Color, commercial enzymes already in the detergent powder were inactivated by heating to 85° C. in a microwave oven and maintaining this temperature for 10 min.
pH: 10.0
Water hardness: 2 mM $CaCl_2$
Washing time: 30 min
Repetitions: 6
Textile: 2 swatches of aged black 100% cotton 5×6 cm
Drying: Tumble dry
Evaluation:

When the surface fibrils and fibers protruding from the yarn are removed by cellulase, the surface of the black fabric appears darker and free from fuzz. A test panel ranks the swatches relative to each other. They are given a number starting with 1 from the "ugliest" and up to 18 for the "nicest" swatch. Swatches with values above 12 have a very improved surface appearance. Swatches with values above 6 have a clearly visible improved surface appearance.

Results:

For each tested strain, three different dosages of cellulase were tested and compared with a blind sample:

|  | S-CEVU/1 | | | |
| --- | --- | --- | --- | --- |
| Strain | 0 | 50 | 100 | 250 |
| Acremonium sp., CBS 478.94 | 2.0 | 12.3 | 14.0 | 15.0 |
| Acremonium sp., CBS 265.95 | 2.0 | 3.0 | 9.7 | 9.0 |

The data show that especially Acremonium sp., CBS 478.94, but also Acremonium sp., CBS 265.95, give very good color clarification in the commercial detergent matrix.

EXAMPLE 5
Performance of Cellulase from Acremonium Strains Measured as Removal of Surface Fibrils and Fibers Protruding from the Yarn of a Textile Containing Cellulosic Fibers
Materials and Methods Apparatus: Terg-o-tometer
Liquid volume: 100 ml
Agitation: 150 movements/min with vertical stirrer
Rinse time: 5 min in tapwater
Washing temp: 40° C.
Washing liquor: 0.05M phosphate buffer
pH: 7.0
Washing time: 30 min
Repetitions: 2
Textile: 2 swatches of aged black 100% cotton 5×6 cm
Drying: Tumble dry
Evaluation:

When the surface fibrils and fibers protruding from the yarn are removed by cellulase, the surface of the black fabric appears darker and free from fuzz. A test panel ranks the swatches relative to each other. They are given a number starting with 1 from the "ugliest" and up to 18 for the "nicest" swatch. Swatches with values above 12 have a very improved surface appeareance.

For each tested strain, two different dosages of Acremonium cellulase were tested and compared with a blind sample:

|  | S-CEVU/1 | | | | |
| --- | --- | --- | --- | --- | --- |
| Strain | 0 | 200 | 500 | 1000 | 2500 |
| A. furatum, CBS 299.70H | 5.5 | 13.0 | n.t. | 18.0 | n.t. |
| A. incoloratum, CBS 146.62 | 5.5 | n.t. | 13.0 | n.t. | 16.0 |

The data show that especially cellulase from Acremonium furatum, CBS 299.70H, but also from Acremonium incoloratum, CBS 146.62 (ATCC 14613), gives very good colour clarification under the test conditions.

In further tests, also cellulases from Acremonium obclavatum, CBS 311.74, Acremonium brachypenium, CBS 866.73, and Acremonium pinkertoniae, CBS 157.70, showed colour clarification under the test conditions.

EXAMPLE 6

Cloning and Expression of a Family 5 Cellulase from Acremonium sp., CBS 265.95

A library from Acremonium sp. CBS 265.95 consisting of approx. $10^6$ individual clones in 50 pools was constructed in E. coli as described.

DNA was isolated from 100 individual clones from the library and subjected to analysis for cDNA insertion. The insertion frequency was found to be >99%. DNA from some of the pools was transformed into yeast, and 50–100 plates containing 250–500 yeast colonies were obtained from each pool.

Endoglucanase-positive colonies were identified and isolated on agar plates with AZCL HE cellulose. cDNA inserts were amplified directly from the yeast colonies and characterized as described in the Materials and Methods section above. The N-terminal and C-terminal DNA sequences, respectively, of the cDNA encoding the endoglucanase is shown in SEQ ID No. 1 and 2.

The cDNA is obtainable from the plasmid in DSM 10076.

The isolated yeast clones were simultaneously tested on agar plates containing AZCL β-glucan, AZCL xyloglucan or AZCL HE cellulose, and found positive on AZCL HE cellulose and AZCL β-glucan.

Total DNA was isolated from a yeast colony and plasmid DNA was rescued by transformation of E. coli as described above. In order to express the endoglucanase in Aspergillus, the DNA was digested with HindIII/XbaI, size fractionated on gel, and a fragment corresponding to the endoglucanase gene was purified. The gene was subsequently ligated to HindIII/XbaI digested pHD414 resulting in the plasmid pA2C346.

After amplification of the DNA in E. coli the plasmid pA2C346 was transformed into Aspergillus oryzae as described above.

Test of A. oryzae Transformants

Each of the transformants were tested for endoglucanase activity as described above. Some of the transformants had endoglucanase activity which was significantly larger than the Aspergillus oryzae background. This demonstrates efficient expression of the endoglucanase in Aspergillus oryzae.

The endoglucanase was determined as being a Family 5 cellulase (determation of family based on the disclosure in Henrissat, B. et al. in *Biochem. J.* Vol. 293, p. 781–788, (1993)) and having a fungal type CBD (cellulose binding domain)at the N-terminal. Fungal type CBD's are described by Gilkes, Henrissat, Kilburn, Miller and Warren in *Microbiological Reviews*, Vol. 55, p. 303–315, (1991).

EXAMPLE 7

Cloning and Expression of a Family 7 Cellulase from Acremonium sp., CBS 265.95

A library from Acremonium sp. CBS 265.95 consisting of approx. $10^6$ individual clones in 50 pools was constructed in E. coli as described.

Cloning and expression was carried out as described in example 6, the resulting plasmid being pA2C347.

The isolated yeast clones were simultaneously tested on agar plates containing AZCL β-glucan, AZCL xyloglucan or AZCL HE cellulose, and found positive on all substrates AZCL HE cellulose, AZCL xyloglucan and AZCL β-glucan.

The DNA sequence of the cDNA encoding the endoglucanase is shown in SEQ ID No. 3.

The cDNA is obtainable from the plasmid in DSM 9969.

The endoglucanase was determined as being a Family 7 cellulase (determation of family based on the disclosure in Henrissat, B. et al. in *Biochem. J.* Vol. 293, p. 781–788, (1993)).

The molecular weight (MW) of the endoglucanase expressed in Aspergillus oryzae was determined to 58 kD in SDS-PAGE.

EXAMPLE 8

Cloning and Expression of a Family 7 Cellulase from Acremonium sp., CBS 478.94

A library from Acremonium sp. CBS 478.94 consisting of approx. $10^6$ individual clones in 50 pools was constructed in E. coli as described.

Cloning and expression was carried out as described in example 6, the resulting plasmid being pA2C349.

The isolated yeast clones were simultaneously tested on agar plates containing AZCL β-glucan, AZCL xyloglucan or AZCL HE cellulose, and found positive on all substrates: AZCL HE cellulose, AZCL xyloglucan and AZCL β-glucan.

The DNA sequence of the cDNA encoding the endoglucanase is shown in SEQ ID No. 4. This sequence showed about 66% identity with the DNA coding for Fusarium oxysporum EG I for 945 bases, cf. Sheppard et al., 1994, Family c endoglucanase.

The cDNA is obtainable from the plasmid in DSM 9977.

The endoglucanase was determined as being a Family 7 cellulase (determation of family based on the disclosure in Henrissat, B. et al. in *Biochem. J.* Vol. 293, p. 781–788, (1993)).

The molecular weight (MW) of the endoglucanase expressed in Aspergillus oryzae was determined to 60 kD in SDS-PAGE.

EXAMPLE 9

Cloning and Expression of a New Cellulase from Acremonium sp., CBS 478.94

A library from Acremonium sp. CBS 478.94 consisting of approx. $10^6$ individual clones in 50 pools was constructed in E. coil as described.

Cloning and expression was carried out as described in example 6, the resulting plasmid being pA2C359.

The isolated yeast clones were simultaneously tested on agar plates containing AZCL β-glucan, AZCL xyloglucan or AZCL HE cellulose, and found positive on only two substrates: AZCL HE cellulose and AZCL xyloglucan.

The DNA sequence of the cDNA encoding the endoglucanase is shown in SEQ ID No. 5.

The cDNA is obtainable from the plasmid in DSM 10077.

The N-termnail showed homology to fungal type CBD's as described by Gilkes, Henrissat, Kilburn, Miller and Warren in *Microbiological Reviews*, Vol. 55, p. 303–315, (1991).

EXAMPLE 10

Cloning and Expression of a Family 5 Cellulase from Acremonium sp., CBS 478.94

A library from Acremonium sp. CBS 478.94 consisting of approx. $10_6$ individual clones in 50 pools was constructed in E. coli as described.

Cloning and expression was carried out as described in example 6, the resulting plasmid being pA2C363.

The isolated yeast clones were simultaneously tested on agar plates containing AZCL β-glucan, AZCL xyloglucan or AZCL HE cellulose, and found positive on 2 substrates: AZCL HE cellulose and AZCL β-glucan.

The DNA sequence of the cDNA encoding the endoglucanase is shown in SEQ ID No. 6.

The cDNA is obtainable from the plasmid in DSM 10079.

The endoglucanase was determined as being a Family 5 cellulase (determation of family based on the disclosure in Henrissat, B. et al. in *Biochem. J.* Vol. 293, p. 781–788, (1993)) and having a fungal type CBD (cellulose binding domain)at the N-terminal. Fungal type CBD's are described by Gilkes, Henrissat, Kilburn, Miller and Warren in *Microbiological Reviews*, Vol. 55, p. 303–315, (1991).

The molecular weight (MW) of the endoglucanase expressed in *Aspergillus oryzae* was determined to 60 kD in SDS-PAGE.

More than 50% relative activity was obtained in the pH range between pH 6.5 to 10 using CMC as substrate.

EXAMPLE 11
Cloning and Expression of a Cellulase from Acremonium sp., CBS 478.94

A library from Acremonium sp. CBS 478.94 consisting of approx. $10^6$ individual clones in 50 pools was constructed in *E. coli* as described.

Cloning and expression was carried out as described in example 6, the resulting plasmid being pA2C369.

The isolated yeast clones were simultaneously tested on agar plates containing AZCL β-glucan, AZCL xyloglucan or AZCL HE cellulose, and found positive on two substrates: AZCL HE cellulose and AZCL xyloglucan.

The partial N-terminal DNA sequence of the cDNA encoding the endoglucanase is shown in SEQ ID No. 7.

The cDNA is obtainable from the plasmid in DSM 10084.

EXAMPLE 12
Performance of Cloned Cellulase from Acremonium sp. Measured as Removal of Surface Fibrils and Fibers Protruding from the Yarn of a Textile Containing Cellulosic Fibers Enzyme: The endoglucanase described in example 10
Apparatus: Terg-o-tometer
Liquid volume: 100 ml
Agitation: 150 movements/min with vertical stirrer
Rinse time: 5 min in tapwater
Washing temp: 40° C.
Water hardness: I) 0 dH II) 1 mM $CaCl_2$=app. 6 dH Washing liquor: I) 0.05M phosphate buffer, pH 7.0 II) 6.5 g/l Ariel Color, pH 10.0, commercial enzymes already in detergent were inactivated by heating to 85° C. in microwave oven, keeping for 10 minutes at this temperature.

Washing time: I) 30 min
II) 20 min
Repetitions: I) 2 cycles
II) 3 cycles

Textiles for evaluation: 2 swatches of aged black 100% cotton 5×6 cm
Drying: Tumble dry
Evaluation:

When the surface fibrils and fibers protruding from the yarn are removed by cellulase, the surface of the black fabric appears darker and free from fuzz. A test panel ranks the swatches relative to each other. They are given a number starting with 1 from the "ugliest" and up to 18 for the "nicest" swatch. Swatches with values above 11 have a very improved surface appearance. Swatches with values above 6 have a clearly visible improved surface appearance.

Two different dosages were tested and compared with a blind sample. Data as panel score units on pre-aged black cotton. The data in-between buffer and detergent cannot be compared directly, as they refer to different experiments with different washing times and different number of repetitions.

| S-CEVU/1: | 0 | 100 | 400 | 500 | 1000 | 2500 |
|---|---|---|---|---|---|---|
| I) Phosphate buffer, pH 7 | 2.5 | n.t. | n.t. | 14.3 | n.t. | 16.8 |
| II) Ariel Color, pH 10 | 2.0 | 6.0 | 11.3 | n.t. | 11.7 | n.t. | n.t. = not tested

The data show that the tested endoglucanase (encoded by the DNA sequence obtainable from the plasmid in *Saccharomyces cerevisiae*, DSM 10079, give good color clarification in both buffer and detergent.

REFERENCES

Ali, B. R. S. et al., "Cellulases and hemicellulases of the anaerobic fungus Piromyces constitute a multiprotein cellulose-binding complex and are encoded by multigene families", FEMS Microbiol. Lett. (1995), Vol. 125, No. 1, pp. 15–21.

Altshul et al., Bull. Math. Bio. Vol 48: 603–616, 1986.

Becker, D. M. & Guarante, L. 1991. Methods Enzymol. 194: 182–187.

Dalbøge, H. and Heldt-Hansen, H. P., "A novel method for efficient expression cloning of fungal enzyme genes", Mol. Gen. Genet. (1994), Vol. 243, pp. 253–260.

Gilkes, Henrissat, Kilburn, Miller and Warren in *Microbiological Reviews*, Vol. 55, p. 303–315, (1991).

Needleman, S. B. and Wunsch, C. D., *Journal of Molecular Biology*, 48: 443–453, 1970.

Gonzáles, R., et al., "Cloning, sequence analysis and yeast expression of the egiI gene from *Trichoderma longibrachiatum*", Appl. Microbiol. Biotechnol. (1992), Vol. 38, pp. 370–375.

Gubler, U. & Hoffman, B. J. 1983. Gene 25: 263–269.

Henikoff and Henikoff, Proc. Natl. Acad. Sci. USA vol 89: 10915–10919, 1992.

Henrissat, B. and Bairoch, A. in *Biochem. J.* Vol. 293, p. 781–788, (1993)).

Rev. Microbiol. (1990), Vol. 44, pp. 219–248.

Henrissat, B., "Cellulases and their interaction with cellulose", Cellulose (1994), Vol. 1, pp. 169–196.

Higuchi R., Krummel B. and Saiki R. K. (1988). A general method of in vitro preparation and specific mutagenesis of DNA fragments: study of protein and DNA interactions. Nucl. Acids Res. 16: 7351–7367.

Kang, M. G., Park, H. M., Kim, Y. S, Lee, J. R., Kim, Y. K., Lee, Y. H.: Abstract from 94th General Meeting, American Society Microbiology, K-112, 1994. Purification and some proterties of carboxymethyl cellulase from alkalophilic Cephalosporium sp RYM 202.

Peberdy, J. F.: Penicillium and Acremonium, (1987), p. 2–4, Plenum Press, New York.

Penttilä, M. et al, (1986) Homology between cellulase gnees of *Trichoderma reesei*: complete nucleotide sequence of the endoglucanase I gene. Gene 45:253–263.

Saloheimo, M. et al, (1988) EGIII, a new endoglucanase from *Trichoderma reesei*: the characterization of both gene and enzyme. Gene 63:11–21.

Sambrook, J., Fritsch, E. F. & Maniatis, T. 1989. Molecular Cloning: A Laboratory Manual. Cold Spring Harbor Lab., Cold Spring Harbor, N.Y.

Saloheimo, A., et al., "A novel, small endoglucnaase gene, eg5, from *Trichoderma reesei* isolated by expression in yeast", Molecular Microbiology (1994), Vol. 13(2), pp. 219–228.

Sanger, F., Nicklen, S. & Coulson, A. R. 1977. Proc. Natl. Acad. Sci. U. S. A. 74: 5463–5467.

Sheppard, P. O., et al., "The use of conserved cellulase family-specific sequences to clone Cellulase homologue cDNAs from *Fusarium oxysporum*, Gene, (1994), Vol. 15, pp. 163–167.

van Arsdell, J. N. et al, (1987) Cloning, characterization, and expression in *Saccharomyces cerevisiae* of endoglucanase I from *Trichoderma reesei*, Bio/Technology 5: 60–64.

Xue, G. et al., "Cloning and expression of multiple cellulase cDNAs from the anaerobic rumen fungus *Neocallimastix patriciarum* in *E. coli*, J. Gen. Microbiol. (1992), Vol. 138, pp. 1413–1420.

Xue, G. et al., "A novel polysaccharide hydrolase cDNA (celD) from *Neocallimastix patriciarum* encoding three multi-functional catalytical domains with high endoglucanase, cellobiohydrolase and xylanase activities", J. Gen. Microbiol. (1992), Vol. 138, pp. 2397–2403.

Zhou, L. et al., "Intronless celB from the anaerobic fungus *Neocallimastix patriciarum* encodes a modular family A endoglucanase", Biochem. J. (1994), Vol. 297, pp. 359–364.

Methods in Enzymology, 1988, Vol. 160, p. 200–391 (edited by Wood, W. A. and Kellogg, S. T.).

T. -M. Enveri, "Microbial Cellulases" in W. M. Fogarty, Microbial Enzymes and Biotechnology, Applied Science Publishers, 183–224 (1983).

Beguin, P. and Aubert, J -P., "The biological degradation of cellulose", FEMS Microbiology Reviews 13 (1994) 25–58.

International Patent Publication WO 93/11249.

International Patent Publication WO 94/14953.

International Patent Publication WO 95/02043.

Ford et al., *Protein Expression and Purification* 2: 95–107, 1991.

Cunningham and Wells, *Science* 244, 1081–1085, 1989).

de Vos et al., *Science* 255: 306–312, 1992.

Smith et al., *J. Mol. Biol.* 224: 899–904, 1992.

Wlodaver et al., *FEBS Lett.* 309: 59–64, 1992.

N. Axelsen et al., *A Manual of Quantitative Immunoelectrophoresis*, Blackwell Scientific Publications, 1973, Chapters 2,3,4 and 23.

---

We claim:

1. A DNA sequence encoding an enzyme exhibiting endoglucanase activity selected from the group consisting of:
   (a) SEQ ID NOs:1–2;
   (b) SEQ ID NO:3;
   (c) SEQ ID NO:4;
   (d) SEQ ID NO:5;
   (e) SEQ ID NO:6;
   (f) a DNA sequence which hybridizes with the same oligonucleotide probe as the DNA sequence of (a)–(e) under conditions of: presoaking in 5×SSC and prehydbridizing for 1 hr. at about 40° C. in a solution of 20% formamide, 5×Denhardt's solution, 50 mM sodium phosphate, pH 6.8, and 50 ,g denatured sonicated calf thymus DNA, followed by hybridization in the same solution supplemented with 100 μM ATP for 18 hrs. at about 40° C., followed by a wash in 0.4×SSC at a temperature of about 45° C.; and
   (g) a DNA sequence having at least 90% homology to the DNA sequence (a)–(e).

2. A recombinant expression vector comprising the DNA sequence of claim 1.

3. A cell comprising the DNA vector of claim 2.

4. The cell of claim 3, where the cell a eukaryotic cell.

5. The cell of claim 4, wherein the cell is is a strain of Aspergillus or Trichoderma.

6. A method of producing an enzyme exhibiting endoglucanase activity, comprising
   (a) culturing de cell of claim 3 under conditions permitting the production of the enzyme, and
   (b) recovering the enzyme from the culture.

7. A DNA sequence encoding an enzyme exhibiting endoglucanase activity comprising a sequence selected from the group consisting of:
   (a) the sequences of SEQ ID NOs: 1–2;
   (b) a DNA sequence which hybridizes with the sequence of SEQ ID NOs: 1–2 under conditions of: presoaking in 5×SSC and prehydbridizing for 1 hr. at about 40° C. in a solution of 20% formamide, 5×Denhardt's solution, 50 mM sodium phosphate, pH 6.8, and 50 μg denatured sonicated calf thymus DNA, followed by hybridization in the same solution supplemented with 100 μM ATP for 18 hrs. at about 40° C., followed by a wash in 0.4×SSC at a temperature of about 45° C.; and
   (c) a DNA sequence hating at least 90% homology to the DNA sequence (a)–(b).

8. The DNA sequence of claim 7 obtainable from the plasmid in *Saccharomyces cerevisiae* DSM 10076.

9. A DNA sequence encoding an enzyme exhibiting endoglucanase activity comprising a sequence selected from the group consisting of:
   (a) the sequence of SEQ ID NO:3;
   (b) a DNA sequence which hybridizes with the sequence of SEQ ID NO:3 under conditions of: presoaking in 5× SSC and prehydbridizing for 1 hr. at about 40° C. in a solution of 20% formamide, 5× Denhardt's solution, 50 mM sodium phosphate, pH 6.8, and 50 μg denatured sonicated calf thymus DNA, followed by hybridization in the same solution supplemented with 100 μM ATP for 18 hrs. at about 40° C., followed by a wash in 0.4×SSC at a temperature of about 45° C.; and
   (c) a DNA sequence having at least 90% homology to the DNA sequence (a)–(b).

10. The DNA sequence of claim 9 obtainable from the plasmid in *Saccharomyces cerevisiae* DSM 9969.

11. A DNA sequence encoding an enzyme exhibiting endoglucanase activity comprising a sequence selected from the group consisting of:
    (a) the sequence of SEQ ID NO:4;
    (b) a DNA sequence which hybridizes with the sequence of SEQ ID NO:4 under conditions of: presoaking in 5× SSC and prehydbridizing for 1 hr. at about 40° C. in a solution of 20% formamide, 5×Denhardt's solution, 50 mM sodium phosphate, pH 6.8, and 50 μg denatured sonicated calf thymus DNA, followed by hybridization in the same solution supplemented with 100 μM ATP for 18 hrs. at about 40° C., followed by a wash in 0.4×SSC at a temperature of about 45° C.; and
    (c) a DNA sequence having at least 90% homology to the DNA sequence (a)–(b).

12. The DNA sequence of claim 11 obtainable from the plasmid in *Saccharomyces cerevisiae* DSM 9977.

13. A DNA sequence encoding an enzyme exhibiting endoglucanase activity comprising a sequence selected from the group consisting of:
    (a) the sequence of SEQ ID NO:5;
    (b) a DNA sequence which hybridizes with the sequence of SEQ ID NO:5 under conditions of: presoaking in 5×SSC ad prehydbridizing for 1 hr. at about 40° C. in a solution of 20% formamide, 5×Denhardt's solution, 50 mM sodium phosphate, pH 6.8, and 50 μg denatured sonicated calf thymus DNA, followed by hybridization in the same solution supplemented with 100 μM ATP for 18 hrs. at about 40° C., followed by a wash in 0.4×SSC at a temperature of about 45° C.; and
    (c) a DNA sequence having at least 90% homology to the DNA sequence (a)–(b).

14. The DNA sequence of claim 13 obtainable from the plasmid in *Saccharomyces cerevisiae* DSM 10077.

15. A DNA sequence encoding an enzyme exhibiting endoglucanase activity comprising a sequence selected from the group consisting of:

(a) the sequence of SEQ ID NO:6;
(b) a DNA sequence which hybridizes with the sequence of SEQ ID NO:6 under conditions of: presoaking in 5×SSC and prehydbridizing for 1 hr. at about 40° C. in a solution of 20% formamide, 5×Denhardt's solution, 50 mM sodium phosphate, pH 6.8, and 50 µg denatured sonicated calf thymus DNA, followed by hybridization in the same solution supplemented with 100 µM ATP for 18 hrs. at about 40° C., followed by a wash in 0.4×SSC at a temperature of about 45° C.; and
(c) a DNA sequence having at least 90% homology to the DNA sequence (a)–(b).

16. The DNA sequence of claim 15 obtainable from the plasmid in *Saccharomyces cerevisiae* DSM 10079.

* * * * *

UNITED STATES PATENT AND TRADEMARK OFFICE

CERTIFICATE OF CORRECTION

PATENT NO. : 5,919,691

DATED : July 6, 1999

INVENTOR(S) : Schülein, et al.

It is certified that error appears in the above-identified patent and that said Letters Patent is hereby corrected as shown below:

Col. 47, line 30, claim 1, delete "50 ,g" and insert --50 µg--

Col. 47, line 45, claim 6, delete "de cell" and insert --the cell--

Signed and Sealed this

Twenty-seventh Day of March, 2001

*Attest:*

NICHOLAS P. GODICI

*Attesting Officer*     *Acting Director of the United States Patent and Trademark Office*